United States Patent
Shakkottai et al.

(10) Patent No.: US 11,382,897 B2
(45) Date of Patent: Jul. 12, 2022

(54) THERAPEUTIC COMBINATION FOR TREATMENT OF CEREBELLAR ATAXIA

(71) Applicant: The Regents of the University of Michigan, Ann Arbor, MI (US)

(72) Inventors: Vikram Shakkottai, Ann Arbor, MI (US); David Bushart, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 46 days.

(21) Appl. No.: 16/182,965

(22) Filed: Nov. 7, 2018

(65) Prior Publication Data

US 2019/0134007 A1  May 9, 2019

Related U.S. Application Data

(60) Provisional application No. 62/582,405, filed on Nov. 7, 2017.

(51) Int. Cl.
| A61K 31/423 | (2006.01) |
| A61P 21/00 | (2006.01) |
| A61K 31/197 | (2006.01) |

(52) U.S. Cl.
CPC .......... *A61K 31/423* (2013.01); *A61K 31/197* (2013.01); *A61P 21/00* (2018.01)

(58) Field of Classification Search
CPC ...... A61K 31/423; A61K 31/197; A61P 21/00
See application file for complete search history.

(56) References Cited

U.S. PATENT DOCUMENTS

| 4,343,789 | A | 8/1982 | Kawata et al. |
| 5,033,252 | A | 7/1991 | Carter |
| 5,052,558 | A | 10/1991 | Carter |
| 5,281,420 | A | 1/1994 | Kelm et al. |
| 5,323,907 | A | 6/1994 | Kalvelage |
| 5,340,591 | A | 8/1994 | Nakano et al. |
| 5,456,923 | A | 10/1995 | Nakamichi et al. |
| 5,700,485 | A | 12/1997 | Berde et al. |
| 5,723,269 | A | 3/1998 | Akagi et al. |
| 6,083,518 | A | 7/2000 | Lindahl |
| 2004/0013734 | A1 | 1/2004 | Babcock et al. |
| 2010/0255093 | A1 | 10/2010 | Edgren et al. |
| 2012/0058992 | A1 | 3/2012 | Cohen et al. |

FOREIGN PATENT DOCUMENTS

| EP | 2397139 A1 * | 12/2011 |
| JP | 2015-160819 | 9/2015 |
| WO | WO 2019/094434 | 5/2019 |

OTHER PUBLICATIONS

Perlman, "Cerebellar Ataxia", Current Treatment Options in Neurology 2000, 2, pp. 215-224.*
Alagem, N, et al. Mechanism of Ba(2+) block of a mouse inwardly rectifying K+ channel: differential contribution by two discrete residues. J Physiol. Jul. 15, 2001;534(Pt. 2):381-93.
Alvina, K, et al. KCa channels as therapeutic targets in episodic ataxia type-2. J Neurosci. May 26, 2010;30(21):7249-57.
Ankri, L, et al. Slice it hot: acute adult brain slicing in physiological temperature. J Vis Exp. Oct. 30, 2014(92):e52068.
Ashizawa, T, et al. Clinical characteristics of patients with spinocerebellar ataxias 1, 2, 3 and 6 in the US; a prospective observational study. Orphanet J Rare Dis. Nov. 13, 2013;8:177.
Bean, BP. The action potential in mammalian central neurons. Nat Rev Neurosci. Jun. 2007;8(6):451-65.
Burright, EN, Clark HB, Servadio A, et al. SCA1 transgenic mice: a model for neurodegeneration caused by an expanded CAG trinucleotide repeat. Cell. Sep. 22, 1995;82(6):937-48.
Cao, Y, et al. Modulation of recombinant small-conductance Ca(2+)-activated K(+) channels by the muscle relaxant chlorzoxazone and structurally related compounds. J Pharmacol Exp Ther. Mar. 2001;296(3):683-9.
Cao, YJ, et al. Modulation of recombinant and native neuronal SK channels by the neuroprotective drug riluzole. Eur J Pharmacol. Aug. 2, 2002;449(1-2):47-54.
Chopra, R, et al. Increased dendritic excitability and calcium-dependent PKC activation: a novel mechanism underlying Purkinje neuron dendritic degeneration in cerebellar ataxias. Ann Neurol. 2016;80(s20):S33-S4.
Coetzee, WA, et al. Molecular diversity of K+ channels. Ann N Y Acad Sci. Apr. 30, 1999;868:233-85.
Coutelier, M, et al. A Recurrent Mutation in CACNA1G Alters Cav3.1 T-Type Calcium-Channel Conduction and Causes Autosomal-Dominant Cerebellar Ataxia. Am J Hum Genet. Nov. 5, 2015;97(5):726-37.
Dell'Orco, JM, et al. Potassium channel dysfunction underlies Purkinje neuron spiking abnormalities in spinocerebellar ataxia type 2. Human Molecular Genetics. 2017.
Dell'Orco, JM, et al. Neuronal Atrophy Early in Degenerative Ataxia is a Compensatory Mechanism to Regulate Membrane Excitability. J Neurosci. Aug. 12, 2015;35(32):11292-307.
Doble, A. The pharmacology and mechanism of action of riluzole. Neurology. Dec. 1996;47(6 Suppl 4):S233-41.
Duarri, A, et al. Mutations in potassium channel kcnd3 cause spinocerebellar ataxia type 19. Ann Neurol. Dec. 2012;72(6):870-80.
Durr, A. Autosomal dominant cerebellar ataxias: polyglutamine expansions and beyond. Lancet Neurol. Sep. 2010;9(9):885-94.
Edgerton, JR, et al. Distinct contributions of small and large conductance Ca2+-activated K+ channels to rat Purkinje neuron function. J Physiol. Apr. 1, 2003;548(Pt1):53-69.
Feil, K, et al. Effect of chlorzoxazone in patients with downbeat nystagmus: a pilot trial. Neurology. Sep. 24, 2013;81(13):1152-8.
Ferrer, I, et al. The Purkinje cell in olivopontocerebellar atrophy. A Golgi and immunocytochemical study. Neuropathol Appl Neurobiol. Feb. 1994;20(1):38-46.
Fogel, BL, et al. Do mutations in the murine ataxia gene TRPC3 cause cerebellar ataxia in humans? Mov Disord. Feb. 2015;30(2):284-6.

(Continued)

*Primary Examiner* — Sahar Javanmard
(74) *Attorney, Agent, or Firm* — Casimir Jones SC; David W. Staple

(57) ABSTRACT

Provided herein are combinations of therapeutic agents useful for the treatment of cerebellar ataxia and methods of use thereof. In particular, embodiments herein baclofen and chlorzoxazone are administered for the treatment of cerebellar ataxia.

14 Claims, 7 Drawing Sheets

(56) References Cited

OTHER PUBLICATIONS

Gao, Z, et al. Cerebellar ataxia by enhanced Ca(V)2.1 currents is alleviated by Ca2+-dependent K+-channel activators in Cacna1a(S218L) mutant mice. J Neurosci. Oct. 31, 2012;32(44):15533-46.
Hansen, ST, et al. Changes in Purkinje cell firing and gene expression precede behavioral pathology in a mouse model of SCA2. Hum Mol Genet. Jan. 15, 2013;22(2):271-83.
Hibino, H, et al. Inwardly rectifying potassium channels: their structure, function, and physiological roles. Physiol Rev. Jan. 2010;90(1):291-366.
Hirono, M, et al. GABA(B) receptor activation enhances mGluR-mediated responses at cerebellar excitatory synapses. Nat Neurosci. Dec. 2001;4(12):1207-16.
Hourez, R, et al. Aminopyridines correct early dysfunction and delay neurodegeneration in a mouse model of spinocerebellar ataxia type 1. J Neurosci. Aug. 17, 2011;31(33):11795-807.
Ilg et al., Consensus Paper: Management of Degenerative Cerebellar Disorders, Cerebellum, Apr. 2014;13(2):248-268.
Jacobi, H, et al. The natural history of spinocerebellar ataxia type 1, 2, 3, and 6: a 2-year follow-up study. Neurology. Sep. 13, 2011;77(11):1035-41.
Jayabal, S, et al. 4-aminopyridine reverses ataxia and cerebellar firing deficiency in a mouse model of spinocerebellar ataxia type 6. Sci Rep. Jul. 6, 2016;6:29489.
Kasumu, AW, et al. Selective positive modulator of calcium-activated potassium channels exerts beneficial effects in a mouse model of spinocerebellar ataxia type 2. Chem Biol. Oct. 26, 2012;19(10):1340-53.
Lee YC, et al. Mutations in KCND3 cause spinocerebellar ataxia type 22. Ann Neurol. Dec. 2012;72(6):859-69.
Liu et al., Stimulatory effects of chlorzoxazone, a centrally acting muscle relaxant, on large conductance calcium-activated potassium channels in pituitary GH3 cells. Brain Res. Jan. 3, 2003;959(1):86-97.
Mercer, AA, et al. Sex differences in cerebellar synaptic transmission and sex-specific responses to autism-linked Gabrb3 mutations in mice. Elife. Apr. 14, 2016,5.
Morino, H, et al. A mutation in the low voltage-gated calcium channel CACNA1G alters the physiological properties of the channel, causing spinocerebellar ataxia. Mol Brain. Dec. 29, 2015;8:89.
Pedarzani, P, et al. Control of electrical activity in central neurons by modulating the gating of small conductance Ca2+-activated K+ channels. J Biol Chem. Mar. 30, 2001;276(13):9762-9.
Power, EM, et al. Prolonged Type 1 Metabotropic Glutamate Receptor Dependent Synaptic Signaling Contributes to Spino-Cerebellar Ataxia Type 1. J Neurosci. May 4, 2016;36(18):4910-6.
Quayle, JM, et al. Inward rectifier K+ currents in smooth muscle cells from rat resistance-sized cerebral arteries. Am J Physiol. Nov. 1993;265(5 Pt 1):C1363-70.
Raman, IM, et al. Ionic currents underlying spontaneous action potentials in isolated cerebellar Purkinje neurons. J Neurosci. Mar. 1, 1999;19(5):1663-74.
Raman, IM, et al. Properties of sodium currents and action potential firing in isolated cerebellar Purkinje neurons. Ann N Y Acad Sci. Apr. 30, 1999;868:93-6.
Rancz, EA, et al. Dendritic spikes mediate negative synaptic gain control in cerebellar Purkinje cells. Proc Natl Acad Sci U S A. Dec. 21, 2010;107(51):22284-9.

Ristori, G, et al. Riluzole in cerebellar ataxia: a randomized, double-blind, placebo-controlled pilot trial. Neurology. Mar. 9, 2010;74(10):839-45.
Romano, S, et al. Riluzole in patients with hereditary cerebellar ataxia: a randomised, double-blind, placebo-controlled trial. Lancet Neurol. Oct. 2015;14(10):985-91.
Sankaranarayanan, A, et al. Naphtho[1,2-d]thiazol-2-ylamine (SKA-31), a new activator of KCa2 and KCa3.1 potassium channels, potentiates the endothelium-derived hyperpolarizing factor response and lowers blood pressure. Mol Pharmacol. Feb. 2009;75(2):281-95.
Sausbier, M, et al. Cerebellar ataxia and Purkinje cell dysfunction caused by Ca2+-activated K+ channel deficiency. Proc Natl Acad Sci U S A. Jun. 22, 2004;101(25):9474-8.
Schmitz-Hubsch, T, et al. Scale for the assessment and rating of ataxia: development of a new clinical scale. Neurology. Jun. 13, 2006;66(11):1717-20.
Sepulveda, FV, et al. Molecular aspects of structure, gating, and physiology of pH-sensitive background K2P and Kir K+-transport channels. Physiol Rev. Jan. 2015;95(1):179-217.
Shakkottai, VG, et al. Enhanced neuronal excitability in the absence of neurodegeneration induces cerebellar ataxia. J Clin Invest. Feb. 2004;113(4):582-90.
Shakkottai, VG, et al. Early changes in cerebellar physiology accompany motor dysfunction in the polyglutamine disease spinocerebellar ataxia type 3. J Neurosci. Sep. 7, 2011;31(36):13002-14.
Shakkottai, VG, et al. FGF14 regulates the intrinsic excitability of cerebellar Purkinje neurons. Neurobiol Dis. Jan. 2009;33(1):81-8.
Shuvaev, AN, et al., Progressive impairment of cerebellar mGluR signalling and its therapeutic potential for cerebellar ataxia in spinocerebellar ataxia type 1 model mice. J Physiol. Jan. 1, 2017;595(1):141-64.
Society TAG. American Geriatrics Society Updated Beers Criteria for Potentially Inappropriate Medication Use in Older Adults. Journal of the American Geriatrics Society. 2012;60:616-31.
Staisch, J, et al. A novel KNCMA1 mutation associated with progressive cerebellar ataxia. Neurology. Apr. 6, 2015,2015;84(14):P2.118.
Tabata, T, et al. GABAergic activation of an inwardly rectifying K+ current in mouse cerebellar Purkinje cells. J Physiol. Mar. 1, 2005;563(Pt 2):443-57.
Van De Leemput, J, et al. Deletion at ITPR1 underlies ataxia in mice and spinocerebellar ataxia 15 in humans. PLoS Genet. Jun. 2007;3(6):e108.
Waters, MF, et al. Mutations in voltage-gated potassium channel KCNC3 cause degenerative and developmental central nervous system phenotypes. Nat Genet. Apr. 2006;38(4):447-51.
Zagha, E, et al. Dendritic Kv3.3 potassium channels in cerebellar purkinje cells regulate generation and spatial dynamics of dendritic Ca2+ spikes. J Neurophysiol. Jun. 2010;103(6):3516-25.
International Search Report and Written Opinion for PCT/US2018/059578, dated Jan. 22, 2019, 10 pages.
Ghaderi Berntsson et al., Hereditary cerebellar ataxia and intrathecal baclofen: A pilot study. Abstract 848. J Neuro Sci. Oct. 15, 2017;381:309.
Extended EP Search Report for EP18875939, dated Jul. 9, 2021, 6 pages.

* cited by examiner

THERAPEUTIC COMBINATION FOR TREATMENT OF CEREBELLAR ATAXIA

CROSS-REFERENCE TO RELATED APPLICATIONS

The present invention claims the priority benefit of U.S. Provisional Patent Application 62/582,405, filed Nov. 7, 2017, which is incorporated by reference in its entirety.

FIELD

Provided herein are combinations of therapeutic agents useful for the treatment of cerebellar ataxia and methods of use thereof. In particular, embodiments herein baclofen and chlorzoxazone are administered for the treatment of cerebellar ataxia.

BACKGROUND

Degenerative cerebellar ataxias are a group of disorders with progressive changes in balance, speech, and gait, often leading to wheelchair confinement. There is a need for agents which improve motor dysfunction in cerebellar ataxia, as there is currently no approved treatment for these debilitating disorders. In mouse models, neuronal dysfunction precedes neuronal loss and occurs with the onset of motor dysfunction (Refs. 1-4; herein incorporated by reference in their entireties). In human autopsy material, in addition to cell loss, morphologically abnormal neurons are consistently present (ref 5; herein incorporated by reference in its entirety). This suggests that neuronal dysfunction may be an important feature of cerebellar ataxia. Defining this neuronal dysfunction represents an outstanding target for treatment of motor dysfunction in cerebellar ataxia.

Spinocerebellar ataxias (SCA) are a group of dominantly inherited disorders affecting the cerebellum and related pathways. The most common SCAs (SCA1, SCA2, SCA3, and SCA6) result from glutamine-encoding repeat expansions in the respective disease-causing genes (Ref 6; herein incorporated by reference in its entirety). Cerebellar Purkinje neuron degeneration is particularly prominent in autopsy tissue from SCA1, SCA2, and SCA6 patients.

SUMMARY

Provided herein are combinations of therapeutic agents useful for the treatment of cerebellar ataxia and methods of use thereof. In particular, embodiments herein baclofen and chlorzoxazone are administered for the treatment of cerebellar ataxia.

In some embodiments, the present invention provides methods of treating a subject suffering from cerebellar ataxia, comprising: co-administering to the subject baclofen and chlorzoxazone. In some embodiments, co-administering results in a reduction of the symptoms of cerebellar ataxia. In some embodiments, co-administering results in a reduction in markers or biomarkers of cerebellar ataxia. In some embodiments, administering results in inhibition of the underlying causes of cerebellar ataxia. In some embodiments, administering results in treatment of cerebellar ataxia. In some embodiments, before treatment the subject has or is at risk of cerebellar ataxia. In some embodiments, the subject is human.

In some embodiments, methods further comprises a step comprising testing the subject for cerebellar ataxia, symptoms thereof, biomarkers thereof, or an underlying cause thereof (e.g., before an/or after treatment). In some embodiments, method further comprises a step of assessing the effectiveness of treatment based upon said testing. In some embodiments, methods further comprise adjusting the treatment based on said assessing. In some embodiments, adjusting the treatment comprises one or more of altering the dose and/or dosing regimen of baclofen and/or chlorzoxazone, adding additional treatment, eliminating an additional treatment, etc.

In some embodiments, a method comprises co-administering a baclofen and chlorzoxazone that are co-formulated in a single pharmaceutical composition. In other embodiments, the baclofen and chlorzoxazone are separate pharmaceutical compositions and are co-administered (e.g., within 1 week, within 6 days, within 5 days, within 4 days, within 3 days, within 2 days, within 1 day, within 12 hours, within 6 house, within 4 hours, within 3 hours, within 2 hours, within 1 hour, within 20 minutes, within 15 minutes, within 5 minutes, within 1 minute, simultaneously, etc.). In some embodiments, the baclofen and chlorzoxazone are both administered orally (e.g., in any suitable oral formulation).

In some embodiments, the present invention provides prescribing or selling baclofen and chlorzoxazone to a subject suffering from cerebellar ataxia. In some embodiments, the baclofen and chlorzoxazone are co-formulated within a single pharmaceutical composition. In some embodiments, the baclofen and chlorzoxazone are separately-formulated within a single pharmaceutical composition. In some embodiments, the baclofen and chlorzoxazone are separate pharmaceutical compositions.

In some embodiments, provided herein is a pharmaceutical composition comprising baclofen and chlorzoxazone. In some embodiments, the baclofen and chlorzoxazone are co-formulated within a single pharmaceutical composition. In some embodiments, the baclofen and chlorzoxazone are separately formulated (e.g., separate release profiles (e.g., quick release, delayed release, enterically-coated, etc.) within a single pharmaceutical composition. In some embodiments, the pharmaceutical composition is suitable for oral administration.

In some embodiments, provided herein is a kit comprising separate baclofen and chlorzoxazone pharmaceutical compositions. In some embodiments, the baclofen pharmaceutical composition and the chlorzoxazone pharmaceutical composition are packaged together. In some embodiments, the baclofen pharmaceutical composition and the chlorzoxazone pharmaceutical composition within separated containers (e.g., vials, bottles, blister packs, etc.) but are packaged together (e.g., same box). In some embodiments, the baclofen and chlorzoxazone are co-formulated within a single pharmaceutical composition. In some embodiments, the baclofen and chlorzoxazone are separately formulated (e.g., separate release profiles (e.g., quick release, delayed release, enterically-coated, etc.) within a single pharmaceutical composition. In some embodiments, the pharmaceutical composition is suitable for oral administration.

DEFINITIONS

Figure 1:
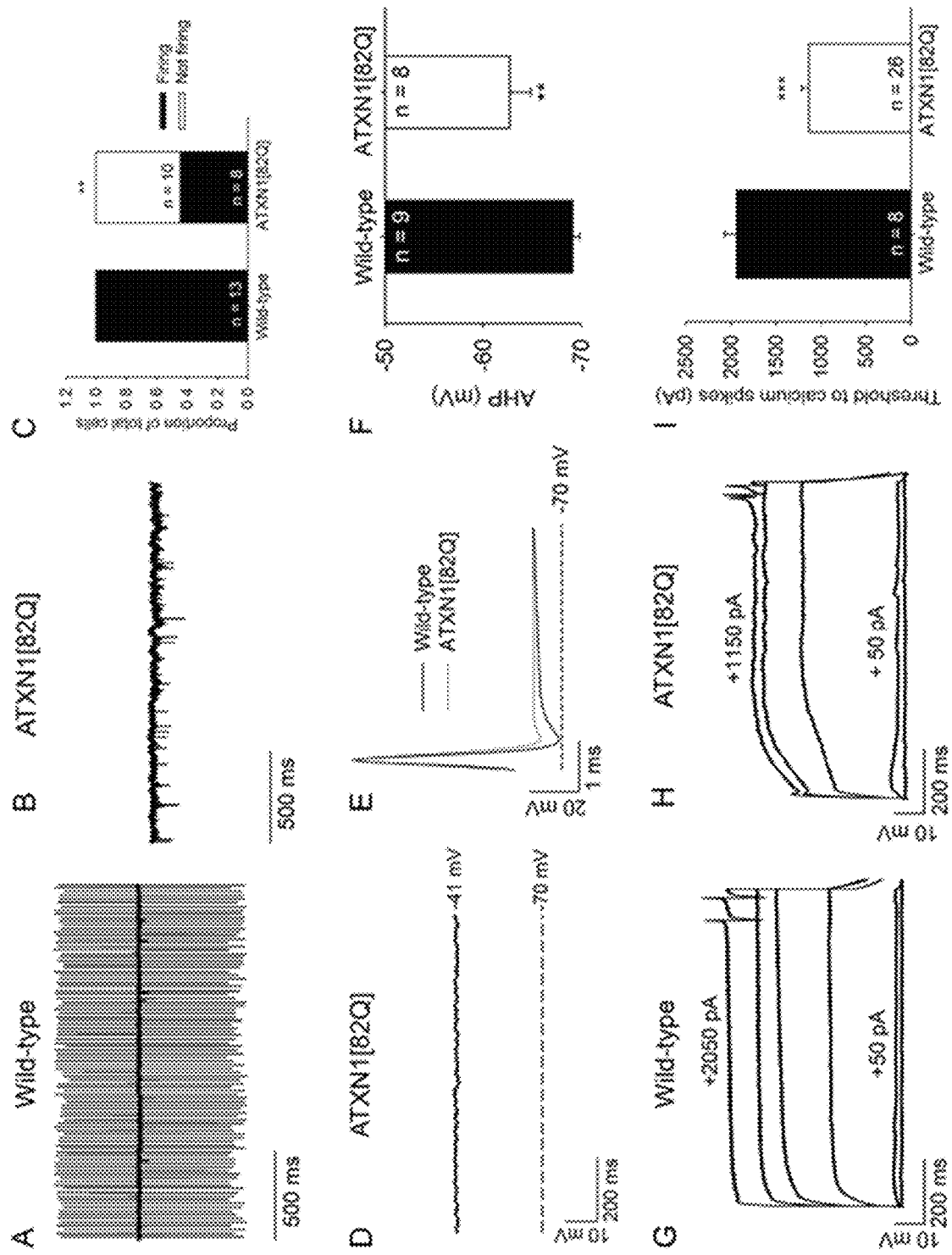
FIG. 1, Panels A-I. ATXN1[82Q] Purkinje neurons display both an absence of repetitive spiking and dendritic hyperexcitability. (Panel A) Representative spiking of a wild-type Purkinje neuron in the cell-attached recording configuration. (Panel B) Representative trace of a non-spiking ATXN1[82Q] Purkinje neuron in the cell-attached recording configuration. (Panel C) Summary of spiking and non-spiking Purkinje neurons from wild-type and ATXN1 [82Q] mice. (Panel D) Representative trace of a non-firing ATXN1[82Q] Purkinje neuron in the whole-cell recording configuration. These neurons display a depolarized resting membrane potential. (Panel E) After-hyperpolarization (AHP) amplitude in wild-type and ATXN1[82Q] Purkinje neurons. (Panel F) Summary of AHP amplitudes in wild-type and ATXN1[82Q] Purkinje neurons. (Panel G) Representative trace of a wild-type Purkinje neuron held at −80 mV in the presence of tetrodotoxin. Upon injection of positive current in +50 pA increments, dendritic calcium spikes are noted. (Panel H) Representative trace of dendritic calcium spike analysis from an ATXN1[82Q] Purkinje neuron. (Panel I) Summary of the threshold of injected current required to elicit dendritic calcium spikes in wild-type and ATXN1[82Q] Purkinje neurons in the presence of tetrodotoxin. *$p<0.05$, $p<0.01$, *$p<0.001$, Fisher's exact test (Panel C) or two-sample Student's t-test (Panel I).

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a compound" is a reference to one or more compounds and equivalents thereof known to those skilled in the art, and so forth.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "subject" refers to any animal including, but not limited to, humans, non-human primates, bovines, equines, felines, canines, pigs, rodents (e.g., mice), and the like. The terms "subject" and "patient" may be used interchangeably, wherein the term "patient" generally refers to a human subject seeking or receiving treatment or preventative measures from a clinician or health care provider.

As used herein, the term "effective amount" refers to the amount of a compound (e.g., a compound having a structure presented above or elsewhere described herein) sufficient to effect beneficial or desired results. An effective amount can be administered in one or more administrations, applications or dosages and is not limited to or intended to be limited to a particular formulation or administration route.

As used herein, the term "co-administration" refers to the administration of at least two agent(s) (e.g., a compound having a structure presented above or elsewhere described herein) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "pharmaceutical composition" refers to the combination of an active agent with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts. Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like. Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $NH^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, the term "instructions for administering said compound to a subject," and grammatical equivalents thereof, includes instructions for using the compositions contained in a kit for the treatment of conditions (e.g., providing dosing, route of administration, decision trees for treating physicians for correlating patient-specific characteristics with therapeutic courses of action).

DETAILED DESCRIPTION

Provided herein are combinations of therapeutic agents useful for the treatment of cerebellar ataxia and methods of use thereof. In particular, embodiments herein baclofen and chlorzoxazone are administered for the treatment of cerebellar ataxia.

Spinocerebellar ataxias (SCA) are a group of dominantly inherited disorders affecting the cerebellum and related pathways. The most common SCAs (SCA1, SCA2, SCA3, and SCA6) result from glutamine-encoding repeat expansions in the respective disease-causing genes (Ref 6; herein incorporated by reference in its entirety). Cerebellar Purkinje neuron degeneration is particularly prominent in autopsy tissue from SCA1, SCA2, and SCA6 patients. In addition, recent studies have demonstrated that Purkinje neuron function is altered at the onset of motor impairment in mouse models of SCA1 and SCA2 (Refs. 1, 2, 4; herein incorporated by reference in their entireties). Coordinated activity of an assortment of ion-channels supports repetitive spiking in Purkinje neurons even in the absence of synaptic input (Refs. 7-9; herein incorporated by reference in their entireties). In mouse models of SCA1-3, a subset of Purkinje neurons exhibit a loss of spontaneous spiking and a depolarized membrane potential early in disease, which is related to reduced function of potassium channels (Refs. 1-3; herein incorporated by reference in their entireties). In addition, potassium channel dysfunction contributes directly to dendritic hyperexcitability in these neurons, which may disrupt dendritic signal integration and contributes to neurodegeneration (Ref 10; herein incorporated by reference in its entirety). Although these studies demonstrate a relationship between altered Purkinje neuron physiology and motor impairment, the role for altered spiking and increased dendritic excitability in causing motor dysfunction is unclear.

Many SCAs are caused by conventional mutations in ion-channel genes (KCNMA1, KCNC3, KCND3, CACNA1A, CACNA1G, ITPR1, SCA8A, TRPC3) (Refs 6, 11-18; herein incorporated by reference in their entireties), and alterations in ion-channel function are secondary to disease-causing mutations in several mouse models of spinocerebellar ataxia (SCA1, SCA2, SCA3, SCA6) (Refs. 1-4, 19; herein incorporated by reference in their entireties). In mouse models of SCA, ion-channel modulators correct irregular Purkinje neuron spiking and improve motor impairment (Refs. 19, 20; herein incorporated by reference in its entirety). Recently, clinical trials for the compound riluzole have demonstrated therapeutic promise for the treatment of several forms of SCA (Refs. 21, 22; herein incorporated by reference in its entirety). The known targets of riluzole include calcium-activated potassium channels, some subthreshold-activated potassium channels, and voltage-gated sodium channels (Refs. 23, 24; herein incorporated by reference in its entirety). It is important to determine which ion-channel targets are relevant for treating symptoms in order to identify effective drugs with reduced potential for off-target effects.

Experiments conducted during development of embodiments herein identify potassium channel modulators which improve Purkinje neuron spiking and dendritic hyperexcitability in SCA1 mice, and indicate that targeting abnormalities in Purkinje neuron spiking alone is an effective short-term therapeutic strategy, but that only a strategy which improves both spiking and dendritic hyperexcitability provides long-term benefit of motor dysfunction in SCA1 mice. Potassium channel modulators that are effective in improving motor dysfunction in the mouse model, and are also approved for human use, are tolerated by patients with SCA and may be effective in improving motor dysfunction in forms of ataxia with prominent Purkinje neuron involvement.

Experiments conducted during development of embodiments herein demonstrate that Purkinje neuron membrane excitability is altered in ATXN1[82Q] mice, and that the resulting changes in physiology can be targeted by potassium channel activators. Experiments illustrate that targeting somatic spiking is only effective for short-term improvements in motor function. Targeting both spiking and dendritic hyperexcitability is associated with sustained improvement in motor dysfunction. Experiments also demonstrate that patients with ataxia can tolerate co-administration of baclofen and chlorzoxazone, and that this combination improves motor dysfunction.

Potassium channel dysfunction may be a feature of many cerebellar ataxias. In mouse models of SCA1, SCA2, and SCA3, alterations in Purkinje neuron spiking are associated with changes in potassium channel function due to either transcriptional downregulation (SCA1 and SCA2) (Refs. 1,2; herein incorporated by reference in their entireties) or altered potassium channel kinetics (SCA3) (Ref 3; herein incorporated by reference in its entirety). Experiments conducted during development of embodiments herein that these changes in potassium channel function in ATXN1 [82Q] mice may be targeted by potassium channel-activating compounds. Not only do potassium channel-activating compounds improve motor dysfunction in a mouse model of SCA1, but also show therapeutic promise in human SCA, and that more than one potassium channel target must be engaged in order to sustain improvements in motor dysfunction.

Previous studies have focused on restoring somatic spiking as an approach to improve motor function in mouse models of ataxia (Refs. 2, 19, 20, 40; herein incorporated by reference in their entireties). Experiments conducted during development of embodiments herein demonstrate that improving Purkinje neuron spiking indeed improves motor performance in the short-term, an effect which has been previously illustrated using $K_{Ca}$ activators in a mouse model of SCA2 (Ref 20; herein incorporated by reference in its entirety). The magnitude of the improvement in motor dysfunction is not to wild-type levels likely due to the inability of these compounds to restore normal firing frequency. However, restoring Purkinje neuron spiking alone is not sufficient to improve motor dysfunction in the long-term. Only compounds which additionally reduce dendritic hyperexcitability provide sustained benefit in a mouse model of SCA1. While $K_{Ca}$ activating-compounds effectively modulate Purkinje neuron spike frequency and regularity, experiments conducted during development of embodiments herein demonstrate that additional engagement of subthreshold-activated potassium channels is necessary for the sustained improvement of motor impairment in ataxia. Experiments illustrate that both baclofen and chlorzoxazone reduce dendritic hyperexcitability in ATXN1[82Q] mice, while SKA-31 does not. Improvement in motor dysfunction was sustained by chlorzoxazone and baclofen even at a time point in ATXN1[82Q] mice when there is significant Purkinje neuron dendritic degeneration. Baclofen and chlorzoxazone both appear to activate different subthreshold-activated potassium channels to reduce Purkinje neuron dendritic hyperexcitability.

Treatment with a combination of chlorzoxazone and baclofen is not only tolerated by SCA patients but also improves symptoms. Experiments conducted during development of embodiments herein demonstrate that chlorzoxazone and baclofen co-administration improves SARA scores in SCAs with prominent Purkinje neuron involvement. This indicates that a common underlying mechanism of disease may be present in SCAs with prominent Purkinje neuron involvement, even if the disease-causing mutation is not directly related to potassium channel function.

Cerebellar ataxia is a form of ataxia originating in the cerebellum. Non-progressive congenital ataxia (NPCA) is a classical presentation of cerebral ataxias. Cerebellar ataxia can occur as a result of many diseases and presents with symptoms of an inability to coordinate balance, gait, extremity and eye movements. Lesions to the cerebellum can cause dyssynergia, dysmetria, dysdiadochokinesia, dysarthria and ataxia of stance and gait. Deficits are observed with movements on the same side of the body as the lesion (ipsilateral). Clinicians often use visual observation of people performing motor tasks in order to look for signs of ataxia. There are many causes of cerebellar ataxia including, among others, gluten ataxia, autoimmunity to Purkinje cells or other neural cells in the cerebellum, CNS vasculitis, multiple sclerosis, infection, bleeding, infarction, tumors, direct injury, toxins (e.g., alcohol), genetic disorders, and an association with statin use. Gluten ataxia accounts for 40% of all sporadic idiopathic ataxias and 15% of all ataxias. In some embodiments, provided herein are compositions, formulations, kits, and methods for the treatment of cerebellar ataxia with any of, or any subset of, the aforementioned symptoms, presentations, underlying causes, etc.

Baclofen (sold under the brand name Lioresal among others) is a medication that has been used to treat spasticity. It is a central nervous system depressant and skeletal muscle relaxant. Baclofen has the a molecular structure of:

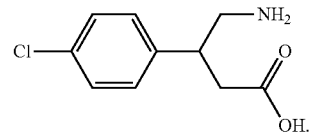 [SMILES: NCC(CC(=O)O)c1ccc(Cl)cc1]

It is a derivative of the neurotransmitter γ-aminobutyric acid (GABA), and is known to function by activating (or agonizing) GABA receptors, specifically the GABAB receptors.

Chlorzoxazone is a centrally acting muscle relaxant used to treat muscle spasm and the resulting pain or discomfort. It acts on the spinal cord by depressing reflexes. It is sold under the trade names Lorzone, Paraflex and Muscol. Side effects include dizziness, lightheadedness, malaise, nausea, vomiting, and liver dysfunction. Chlorzoxazone has the a molecular structure of:

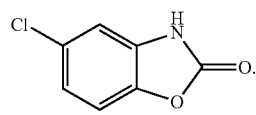 [SMILES: O=c1[nH]c2cc(Cl)ccc2o1]

Baclofen and chlorzoxazone are both known to increase sedation and drowsiness and there are indications that use of the drugs together may increase negative side effects such as dizziness, drowsiness, confusion, and difficulty concentrating.

In some embodiments, the present invention provides methods of treating a subject suffering from cerebellar ataxia, comprising co-administering to the subject baclofen and chlorzoxazone. In some embodiments, an amount of baclofen and chlorzoxazone that is effective in treating cerebellar ataxia is administered. In some embodiments, the dose of baclofen and/or chlorzoxazone would be ineffective in treating cerebellar ataxia alone. In some embodiments, co-administering results in a reduction of the symptoms of cerebellar ataxia, reduction in markers and/or biomarkers of cerebellar ataxia, inhibition of the underlying causes of cerebellar ataxia, and/or treatment of cerebellar ataxia. In some embodiments, before treatment the subject has or is at risk of cerebellar ataxia. In some embodiments, the subject is human. In some embodiments, the baclofen and chlorzoxazone are co-formulated in a single pharmaceutical composition. In other embodiments, the baclofen and chlorzoxazone are separate pharmaceutical compositions and are co-administered (e.g., within 1 week, within 6 days, within 5 days, within 4 days, within 3 days, within 2 days, within 1 day, within 12 hours, within 6 house, within 4 hours, within 3 hours, within 2 hours, within 1 hour, within 20 minutes, within 15 minutes, within 5 minutes, within 1 minute, simultaneously, etc.). In some embodiments, the baclofen and chlorzoxazone are both administered orally (e.g., in any suitable oral formulation).

In some embodiments, the present invention provides prescribing or selling baclofen and chlorzoxazone to a subject suffering from cerebellar ataxia. In some embodiments, the baclofen and chlorzoxazone are co-formulated within a single pharmaceutical composition. In some embodiments, the baclofen and chlorzoxazone are separately-formulated within a single pharmaceutical composition. In some embodiments, the baclofen and chlorzoxazone are separate pharmaceutical compositions.

In some embodiments, methods further comprises a step comprising testing the subject for cerebellar ataxia, symptoms thereof, biomarkers thereof, or an underlying cause thereof (e.g., before an/or after treatment). In some embodiments, method further comprises a step of assessing the effectiveness of treatment based upon said testing. In some embodiments, methods further comprise adjusting the treatment based on said assessing. In some embodiments, adjusting the treatment comprises one or more of altering the dose and/or dosing regimen of baclofen and/or chlorzoxazone, adding additional treatment, eliminating an additional treatment, etc.

In some embodiments, provided herein is a pharmaceutical composition comprising baclofen and chlorzoxazone. In some embodiments, the baclofen and chlorzoxazone are co-formulated within a single pharmaceutical composition. In some embodiments, the baclofen and chlorzoxazone are separately formulated (e.g., separate release profiles (e.g., quick release, delayed release, enterically-coated, etc.) within a single pharmaceutical composition. In some embodiments, the pharmaceutical composition is suitable for oral administration. In some embodiments, provided herein is the use of such pharmaceutical compositions for the treatment of cerebellar ataxia.

In some embodiments, provided herein is a kit comprising separate baclofen and chlorzoxazone pharmaceutical compositions. In some embodiments, the baclofen pharmaceutical composition and the chlorzoxazone pharmaceutical composition are packaged together. In some embodiments, the baclofen pharmaceutical composition and the chlorzoxazone pharmaceutical composition within separated containers (e.g., vials, bottles, blister packs, etc.) but are packaged together (e.g., same box). In some embodiments, the baclofen and chlorzoxazone are co-formulated within a single pharmaceutical composition. In some embodiments, the baclofen and chlorzoxazone are separately formulated (e.g., separate release profiles (e.g., quick release, delayed release, enterically-coated, etc.) within a single pharmaceutical composition. In some embodiments, the pharmaceutical composition is suitable for oral administration. In some embodiments, provided herein is the use of such kits for the treatment of cerebellar ataxia.

In certain embodiments, baclofen and chlorzoxazone are combined with one or more additional agents to form pharmaceutical compositions. Pharmaceutical compositions may be formulated in a conventional manner using one or more physiologically acceptable carriers including excipients and auxiliaries which facilitate processing of the active compound(s) (e.g., baclofen and/or chlorzoxazone) into preparations which can be used pharmaceutically. Proper formulation is dependent upon the route of administration chosen. Additional details about suitable excipients for pharmaceutical compositions described herein may be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

A pharmaceutical composition, as used herein, refers to a mixture of a compound or compounds described herein (e.g., baclofen and/or chlorzoxazone) with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of combinations of baclofen and chlorzoxazone are administered in a pharmaceutical composition or multiple pharmaceutical compositions to a mammal (e.g., human) having a disease, disorder, or condition to be treated (e.g., cerebellar ataxia). In some embodiments, the mammal is a human. A therapeutically effective amount can vary widely depending on the severity of the disease, the age and relative health of the subject, and other factors. Baclofen and chlorzoxazone can be formulated and/or administered singly or in conccurently with one or more additional therapeutic agents.

Pharmaceutical compositions including baclofen and/or chlorzoxazone may be manufactured in a conventional manner, such as, by way of example only, by means of conventional mixing, dissolving, granulating, dragee-making, levigating, emulsifying, encapsulating, entrapping or compression processes.

In some embodiments, the pharmaceutical compositions will include at least one of baclofen or chlorzoxazone as an active ingredient in free-acid or free-base form, or in a pharmaceutically acceptable salt form.

Pharmaceutical preparations for oral use can be obtained by mixing one or more solid excipients with baclofen and/or chlorzoxazone optionally grinding the resulting mixture, and processing the mixture of granules, after adding suitable auxiliaries, if desired, to obtain tablets, pills, or capsules. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

In some embodiments, dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds (e.g., baclofen and/or chlorzoxazone) are dissolved or suspended in suitable liquids, such as fatty oils, liquid paraffin, or liquid polyethylene glycols. In addition, stabilizers may be added.

In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder), a capsule (including both soft or hard capsules, e.g., capsules made from animal-derived gelatin or plant-derived HPMC, or "sprinkle capsules"), solid dispersion, solid solution, bioerodible dosage form, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations of baclofen and/or chlorzoxazone may be administered as a single capsule or in multiple capsule dosage form. In some embodiments, the pharmaceutical formulation is administered in two, or three, or four, capsules or tablets.

In some embodiments, solid dosage forms, e.g., tablets, effervescent tablets, and capsules, are prepared by mixing particles of a baclofen and/or chlorzoxazone (and/or other active ingredients) with one or more pharmaceutical excipients to form a bulk blend composition. When referring to these bulk blend compositions as homogeneous, it is meant that the particles of the compound described herein are dispersed evenly throughout the composition so that the composition may be subdivided into equally effective unit dosage forms, such as tablets, pills, and capsules. The individual unit dosages may also include film coatings, which disintegrate upon oral ingestion or upon contact with diluent. These formulations can be manufactured by conventional pharmacological techniques.

The pharmaceutical solid dosage forms described herein can include a baclofen and/or chlorzoxazone (and/or other active ingredients) and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in Remington's Pharmaceutical Sciences, 20th Edition (2000), a film coating is provided around the formulation of the compound described herein. In one embodiment, some or all of the particles of the compound described herein are coated. In another embodiment, some or all of the particles of the active ingredient(s) (e.g., baclofen and/or chlorzoxazone (and/or other active ingredients)) are microencapsulated. In still another embodiment, the particles of the the active ingredient(s) (e.g., baclofen and/or chlorzoxazone (and/or other active ingredients)) are not microencapsulated and are uncoated.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

In order to release the active agents (e.g., baclofen and/or chlorzoxazone (and/or other active ingredients)) from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or AMIJEL, or sodium starch glycolate such as PROMOGEL or EXPLOTAB, a cellulose such as a wood product, methylcrystalline cellulose, e.g., AVICEL, AVICEL PH101, AVICEL PH102, AVICEL PH105, ELCEMA P100, EMCOCEL, VIVACEL, MING TIA, and SOLKA-FLOC, methylcellulose, croscarmellose, or a cross-linked cellulose, such as cross-linked sodium carboxymethylcellulose (AC-DI-SOL), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., METHOCEL), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropylcellulose (e.g., KLUCEL), ethylcellulose (e.g., ETHOCEL), and microcrystalline cellulose (e.g., AVICEL), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., DIPAC), glucose, dextrose, molasses, mannitol, sorbitol, xylitol (e.g., XYLITAB), lactose, a natural or synthetic gum such as acacia, tragacanth, ghatti gum, mucilage of isapol husks, starch, polyvinylpyrrolidone (e.g., POVIDONE CL, KOLLIDON CL, POLYPLASDONE® XL-10, and POVIDONE K-12), larch arabogalactan, VEEGUM, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. In some embodiments, formulators determine the binder level for the formulations, but binder usage level of up to 70% in tablet formulations is common.

Suitable lubricants or glidants for use in the solid dosage forms described herein include, but are not limited to, stearic acid, calcium hydroxide, talc, corn starch, sodium stearyl fumarate, alkali-metal and alkaline earth metal salts, such as aluminum, calcium, magnesium, zinc, stearic acid, sodium stearates, magnesium stearate, zinc stearate, waxes, STEAROWET, boric acid, sodium benzoate, sodium acetate, sodium chloride, leucine, a polyethylene glycol or a methoxypolyethylene glycol such as CARBOWAX, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., POLYQUAT 10), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., PLURONIC (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 5400 to about 7000, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

There is considerable overlap between additives used in the solid dosage forms described herein. Thus, the above-listed additives should be taken as merely exemplary, and not limiting, of the types of additives that can be included in solid dosage forms of the pharmaceutical compositions described herein.

In other embodiments, one or more layers of the pharmaceutical formulation are plasticized. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

Compressed tablets are solid dosage forms prepared by compacting the bulk blend of the formulations described above. In various embodiments, compressed tablets which are designed to dissolve in the mouth will include one or more flavoring agents. In other embodiments, the compressed tablets will include a film surrounding the final compressed tablet. In some embodiments, the film coating aids in patient compliance (e.g., OPADRY coatings or sugar coating). Film coatings including OPADRY typically range from about 1% to about 3% of the tablet weight. In other embodiments, the compressed tablets include one or more excipients.

A capsule may be prepared, for example, by placing the bulk blend of the formulation(s) (e.g., comprising baclofen and/or chlorzoxazone (and/or other active ingredients)), inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles of baclofen and/or chlorzoxazone (and/or other active ingredients) and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In another aspect, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials compatible with baclofen and/or chlorzoxazone (and/or other active ingredients), which sufficiently isolate the active agent(s) from other non-compatible excipients.

In still other embodiments, effervescent powders are also prepared in accordance with the present disclosure. Effervescent salts have been used to disperse medicines in water for oral administration. Effervescent salts are granules or coarse powders containing a medicinal agent in a dry mixture, usually composed of sodium bicarbonate, citric acid and/or tartaric acid. When such salts are added to water, the acids and the base react to liberate carbon dioxide gas, thereby causing "effervescence." Examples of effervescent salts include, e.g., the following ingredients: sodium bicarbonate or a mixture of sodium bicarbonate and sodium carbonate, citric acid and/or tartaric acid. Any acid-base combination that results in the liberation of carbon dioxide can be used in place of the combination of sodium bicarbonate and citric and tartaric acids, as long as the ingredients were suitable for pharmaceutical use and result in a pH of about 6.0 or higher.

In other embodiments, the formulations described herein, which include a baclofen and/or chlorzoxazone (and/or other active ingredients) are solid dispersions. Methods of producing such solid dispersions include, but are not limited to, for example, U.S. Pat. Nos. 4,343,789, 5,340,591, 5,456,923, 5,700,485, 5,723,269, and U.S. patent publication no. 2004/0013734. In still other embodiments, the formulations described herein are solid solutions. Solid solutions incorporate a substance together with the active agent and other excipients such that heating the mixture results in dissolution of the drug and the resulting composition is then cooled to provide a solid blend which can be further formulated or directly added to a capsule or compressed into a tablet. Methods of producing such solid solutions include, but are not limited to, for example, U.S. Pat. Nos. 4,151,273, 5,281,420, and 6,083,518.

In some embodiments, pharmaceutical formulations are provided that include particles of the baclofen and/or chlorzoxazone (and/or other active ingredients) and at least one dispersing agent or suspending agent for oral administration to a subject. The formulations may be a powder and/or granules for suspension, and upon admixture with water, a substantially uniform suspension is obtained.

Liquid formulation dosage forms for oral administration can be aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002).

The aqueous suspensions and dispersions described herein can remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In one embodiment, an aqueous suspension can be re-suspended into a homogenous suspension by physical agitation lasting less than 1 minute. In another embodiment, an aqueous suspension can be re-suspended into a homogenous suspension by physical agitation lasting less than 45 seconds. In yet another embodiment, an aqueous suspension can be re-suspended into a homogenous suspension by physical agitation lasting less than 30 seconds. In still another embodiment, no agitation is necessary to maintain a homogeneous aqueous dispersion.

The pharmaceutical compositions described herein may include sweetening agents such as, but not limited to, acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sucralose, sorbitol, swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof.

Generally, an agent, such as baclofen and/or chlorzoxazone (and/or other active ingredients), is administered in an amount effective for amelioration of, or prevention of the development of symptoms of, cerebellar ataxia (i.e., a therapeutically effective amount). Thus, a therapeutically effective amount can be an amount that is capable of at least partially preventing or reversing cerebellar ataxia. The dose required to obtain an effective amount may vary depending on the agent, formulation, disease or disorder, and individual to whom the agent is administered.

Determination of effective amounts may also involve in vitro assays in which varying doses of agent are administered to cells in culture and the concentration of agent effective for ameliorating some or all symptoms is determined in order to calculate the concentration required in vivo. Effective amounts may also be based in in vivo animal studies.

An agent can be administered prior to, concurrently with and/or subsequent to the appearance of symptoms of cerebellar ataxia. In some embodiments, an agent is administered to a subject with a family history of the disease, or who has a phenotype that may indicate a predisposition to cerebellar ataxia, or who has a genotype which predisposes the subject to the disease.

The pharmaceutical and/or therapeutic formulations, which can conveniently be presented in unit dosage form, can be prepared according to conventional techniques well known in the pharmaceutical/nutriceutical industries. Such techniques include the step of bringing into association the active ingredients (baclofen and/or chlorzoxazone) with the pharmaceutical carrier(s) or excipient(s). In general the formulations are prepared by uniformly and intimately bringing into association the active ingredients with liquid carriers or finely divided solid carriers or both, and then, if necessary, shaping the product. The compositions of the present invention can be formulated into any of many possible dosage forms such as, but not limited to, tablets, capsules, liquid syrups, soft gels, suppositories, and enemas. The compositions of the present invention can also be formulated as suspensions in aqueous, non-aqueous, oil-based, or mixed media. Suspensions can further contain substances that increase the viscosity of the suspension including, for example, sodium carboxymethylcellulose, sorbitol and/or dextran. The suspension can also contain stabilizers. In one embodiment of the present invention the pharmaceutical compositions can be formulated and used as foams. Pharmaceutical foams include formulations such as, but not limited to, emulsions, microemulsions, creams, jellies and liposomes. While basically similar in nature these formulations vary in the components and the consistency of the final product.

The pharmaceutical compositions described herein (e.g., comprising baclofen and/or chlorzoxazone) may be in unit dosage forms suitable for single administration of precise dosages. In unit dosage form, the formulation is divided into unit doses containing appropriate quantities of baclofen and/or chlorzoxazone. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition.

Dosing and administration regimes are tailored by the clinician, or others skilled in the pharmacological arts, based upon well-known pharmacological and therapeutic considerations including, but not limited to, the desired level of therapeutic effect, and the practical level of therapeutic effect obtainable. Generally, it is advisable to follow well-known pharmacological principles for administrating therapeutic agents. In certain embodiments, the compounds are administered to a subject at a dose of about 0.01 mg/kg to about 200 mg/kg, more preferably at about 0.1 mg/kg to about 100 mg/kg, even more preferably at about 0.5 mg/kg to about 50 mg/kg. Dosing may be once per day or multiple times per day for one or more consecutive days.

Provided herein are methods for combination therapies (e.g., co-administering baclofen and chlorzoxazone (and optionally other active agents)). In general, the compositions described herein do not have to be administered in the same pharmaceutical composition. The determination of the mode of administration and the advisability of administration, where possible, in the same pharmaceutical composition, is within the knowledge of the clinician. The initial administration can be made according to established protocols recognized in the field, and then, based upon the observed effects, the dosage, modes of administration and times of administration can be modified by the clinician.

In addition, baclofen and chlorzoxazone also may be used in combination with procedures that may provide additional or synergistic benefit to the patient.

For use in the therapeutic applications described herein, kits and articles of manufacture are also provided. In some embodiments, such kits comprise a carrier, package, or container that is compartmentalized, each of the compartments comprising one of the separate elements to be used in a method described herein (e.g., baclofen, chlorzoxazone, other active agent(s)). Suitable containers include, for example, blister packs, boxes, bottles, vials, syringes, test tubes. The containers are formed from a variety of materials such as glass or plastic.

The articles of manufacture provided herein contain packaging materials. Packaging materials for use in packaging pharmaceutical products include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, the container(s) includes baclofen and/or chlorzoxazone optionally in a composition or in combination. Such kits optionally comprising a an identifying description or label or instructions relating to its use in the methods described herein.

The technology herein also relates to methods of treatment with baclofen and chlorzoxazone. According to another aspect of the technology, a method is provided for treating a subject suffering from cerebellar ataxia with an effective amount of an baclofen and chlorzoxazone (in a single or multiple formulations or compositions). The method involves co-administering to the subject an effective amount of baclofen and chlorzoxazone in any of the pharmaceutical preparations described above, detailed herein, and/or set forth in the claims. The subject can be any subject in need of such treatment.

In some embodiments, provided herein are methods of treating cerebellar ataxia comprising co-administering a pharmaceutically effective amount of baclofen and chlorzoxazone to a subject having a condition in need of treatment. In some embodiments, the administration causes one or more of: a reduction in or elimination of one or more symptoms of cerebellar ataxia, prevention of increased severity of one or more symptoms of cerebellar ataxia, and/or reduction, prevention, or elimination of cerebellar ataxia.

In some embodimentts, the methods provided comprise testing a subject for cerebellar ataxia followed by administering a baclofen and chlorzoxazone. In some embodiments, methods comprise administering to a subject a baclofen and chlorzoxazone followed by testing the subject for a cerebellar ataxia. In some embodiments, methods comprise testing a subject for cerebellar ataxia followed by administering baclofen and chlorzoxazone, followed by a second round of testing for cerebellar ataxia (e.g., to monitor the effect of the treatment). In some embodiments, methods comprise testing a subject for cerebellar ataxia followed by administering baclofen and chlorzoxazone, followed by a second round of testing for cerebellar ataxia and a second administration of baclofen and chlorzoxazone, with this second administration being modified in dose, duration, frequency, or administration route in a manner dependent upon the results of the prior testing. In some embodiments, a subject is tested to assess the presence, the absence, or the level of baclofen and chlorzoxazone, e.g., by assaying or measuring a biomarker, a metabolite, a physical symptom, an indication, etc., to determine the risk of or the presence of the disease and thereafter the subject is treated with baclofen and chlorzoxazone based on the outcome of the test. In some embodiments, a patient is tested, treated, and then tested again to monitor the response to therapy. In some embodiments, cycles of testing and treatment may occur without limitation to the pattern of testing and treating (e.g., test/treat, test/treat/test, test/treat/test/treat, test/treat/test/treat/test, test/treat/treat/test/treat/treat, etc.), the periodicity, or the duration of the interval between each testing and treatment phase.

In some embodiments, the technology provided comprises use of baclofen and chlorzoxazone in the manufacture of a medicament for the treatment of cerebellar ataxia. In some embodiments, the technology provides baclofen and chlorzoxazone for the treatment of cerebellar ataxia.

EXPERIMENTAL

Methods

Mice

Animal procedures were approved by the University of Michigan Committee on the Use and Care of Animals, and were conducted in accordance with the United States Public Health Service's Policy on Human Care and Use of Laboratory Animals. Homozygous ATXN1[82Q] transgenic mice (ref 25; herein incorporated by reference in its entirety), which overexpress human ATXN1 with 82 CAG repeats selectively in cerebellar Purkinje neurons under the Pcp2 promotor, were maintained on an FVB background. Wild-type FVB mice (Jackson Labs) were used as controls for all experiments. Data presented from these experiments were from mice at either 5 weeks of age or 14 weeks of age. Sexes were balanced for animal studies. For studies involving animals, an uppercase "N" denotes the number of mice used per group, while a lowercase "n" denotes the number of cells used per group.

Patch-Clamp Electrophysiology: Solutions

Artificial CSF (aCSF) contained the following (in mM): 125 NaCl, 3.8 KCl, 26 NaHCO$_3$, 1.25 NaH$_2$PO$_4$, 2 CaCl$_2$, 1 MgCl$_2$, and 10 glucose. For sections made at 4° C., cutting solution contained the following (in mM): 87 NaCl, 2.5 KCl, 25 NaHCO$_3$, 1 NaH$_2$PO$_4$, 0.5 CaCl$_2$, 7 MgCl$_2$, 75 sucrose, and 10 glucose. Unless otherwise specified, pipettes were filled with an internal recording solution containing the following (in mM): 119 K Gluconate, 2 Na gluconate, 6 NaCl, 2 MgCl$_2$, 0.9 EGTA, 10 HEPES, 14 Tris-phosphocreatine, 4 MgATP, 0.3 tris-GTP, pH 7.3, osmolarity 290 mOsm. In order to block potassium channels in some dendritic excitability experiments, pipettes were filled with an internal recording solution containing the following (in mM): 140 CsCl, 2 MgCl$_2$, 1 CaCl$_2$, 10 EGTA, 10 HEPES, 4 Na$_2$ATP, pH 7.3, osmolarity 287 mOsm.

Patch-Clamp Electrophysiology: Reagents

Baclofen (Sigma Aldrich, Cat. No. B5399) was used at 10 μM for studies involving somatic spiking, and at 2 μM for experiments assessing dendritic excitability. Chlorzoxazone (Sigma Aldrich, Cat. No. C4397) was used at 50 μM for all in vitro experiments. SKA-31 was synthesized in-house and was used at 10 μM for all in vitro experiments. 1-EBIO (Tocris, Cat. No 1041) was used at 100 μM for all experiments. Barium chloride (Sigma Aldrich, Cat. No. 217565) was used at 50 μM or 500 μM to block subthreshold-activated potassium channels. Cadmium chloride (Sigma Aldrich, Cat. No. C3141) was used at 100 μM to block voltage-gated calcium channels. Tetrodotoxin (Alomone Labs, Cat. No. T-550) was used at 1 μM. During some assessments of dendritic excitability, U-73122 (Tocris, Cat. No. 1268) was added to the internal pipette solution at a concentration of 10 μM to inhibit phospholipase C.

Acute Slice Preparation for Electrophysiological Recordings

Figure 2:
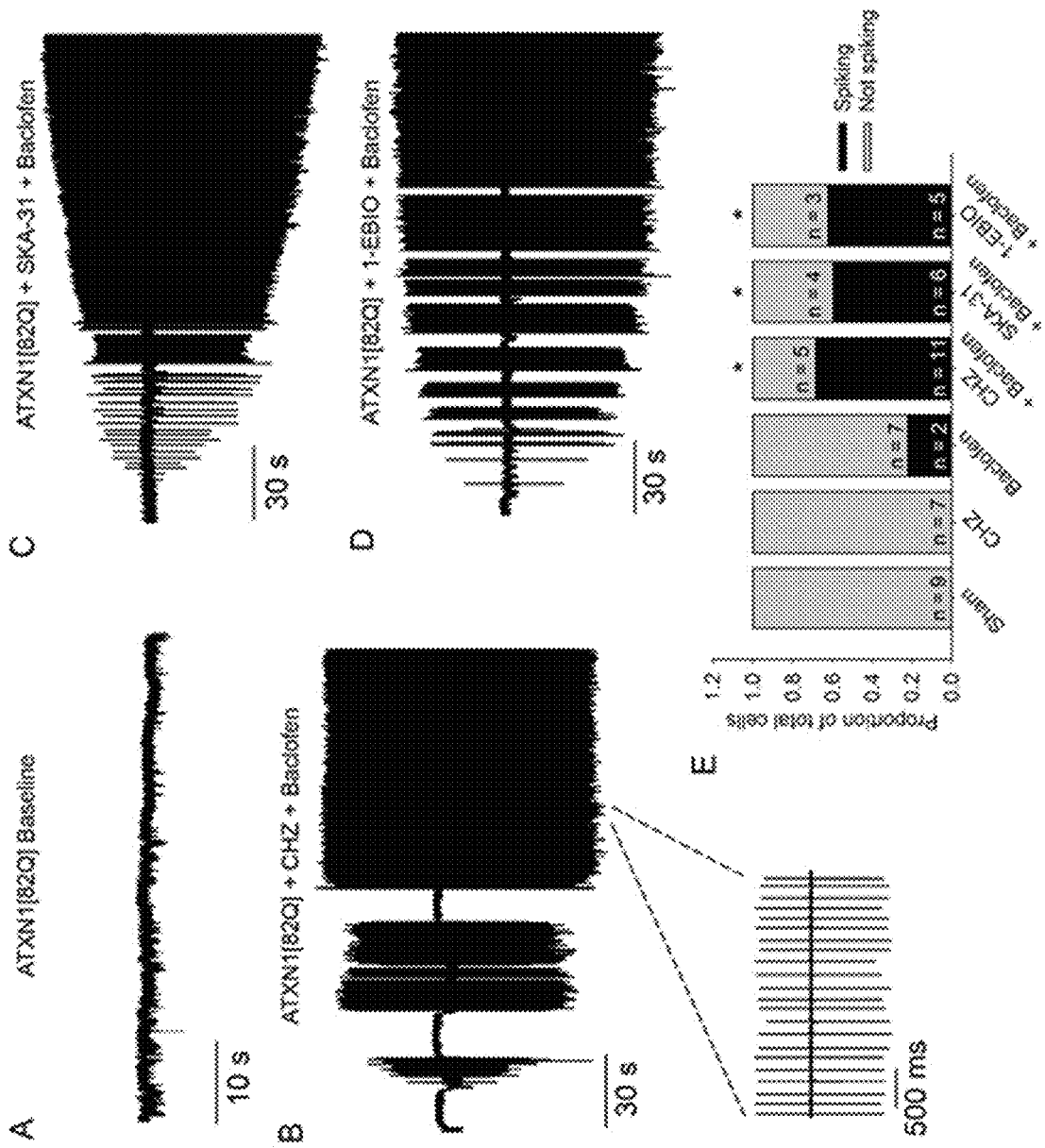
FIG. 2, Panels A-E. Potassium channel-activating compounds restore spiking in non-firing ATXN1[82Q] Purkinje neurons. (Panel A) In a cell-attached recording configuration, the majority of ATXN1[82Q] Purkinje neurons are non-firing at 5 weeks of age. (Panel B) Co-application of chlorzoxazone (CHZ, 50 µM) and baclofen (10 µM) restores repetitive spiking to non-firing ATXN1[82Q] Purkinje neurons ($p=0.001$). Inset of restored spiking with chlorzoxazone and baclofen is shown on an expanded time scale. (Panel C) SKA-31 (10 µM) and baclofen (10 µM) co-application also restores spiking to non-firing ATXN1[82Q] Purkinje neurons ($p=0.01$), as does (Panel D) 1-EBIO (100 µM) and baclofen (10 µM) ($p=0.009$). (Panel E) Summary of data from figures B-D. *adjusted $p<0.01$ when compared to sham, Fisher's exact test with Bonferroni post-correction (required p 0.05/5=0.01).
Figure 3:
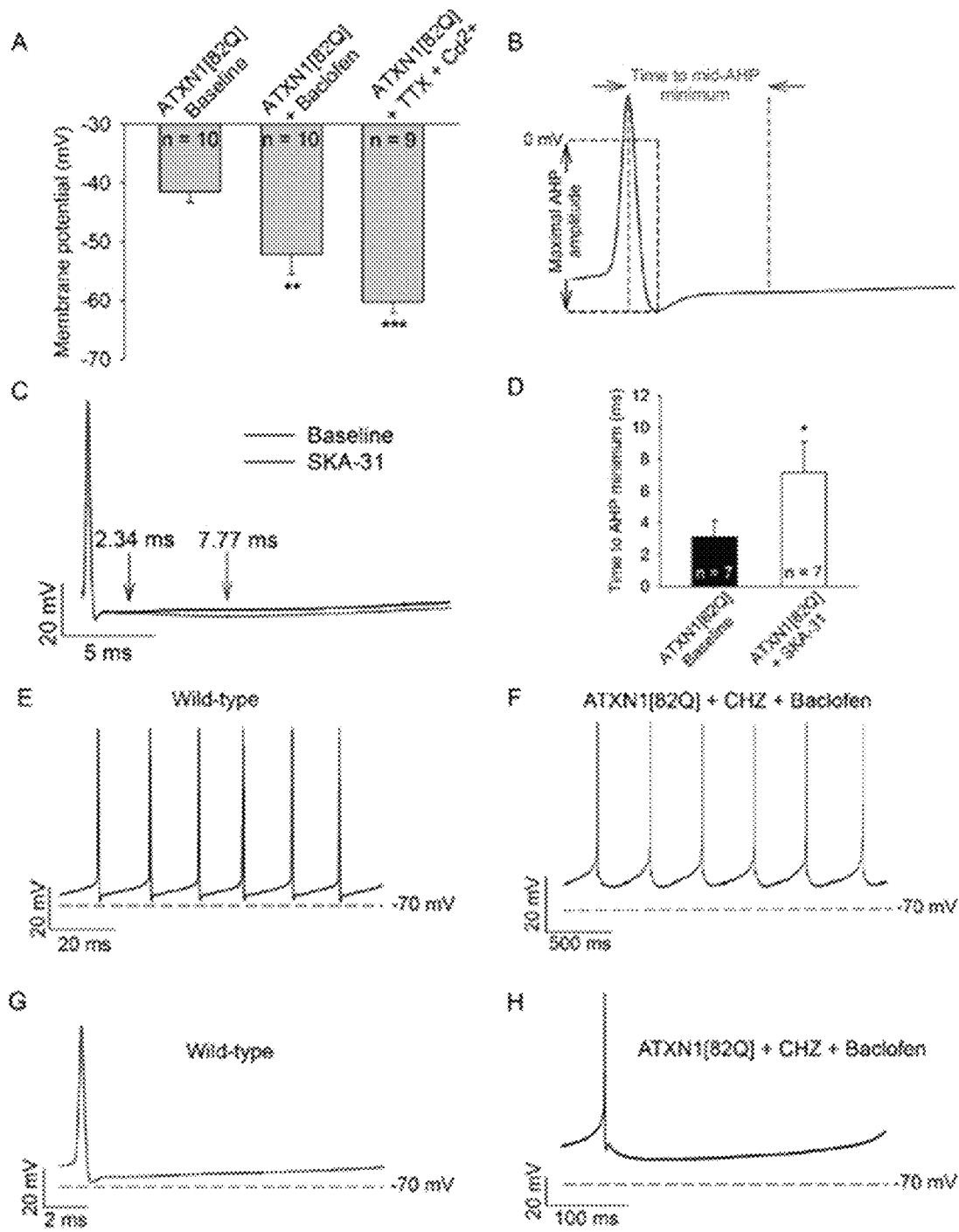
FIG. 3, Panels A-H. $K_{Ca}$ activators and baclofen enhance the AHP and repolarize the membrane potential of ATXN1 [82Q] Purkinje neurons. (Panel A) Baclofen (10 µM) hyperpolarizes the membrane potential of depolarized ATXN1 [82Q] Purkinje neurons to from −41 mV to −52 mV. Tetrodotoxin (1 µM) and cadmium (100 µM) repolarizes the membrane potential to −60 mV. (Panel B) Protocol for analysis of the time to minimal mid-AHP and maximal AHP amplitude. (Panel C) Representative trace of the AHP of an ATXN1[82Q] Purkinje neuron before (black trace) and after (red trace) SKA-31 perfusion (10 µM). The time to slow AHP minimum is denoted by arrows. (Panel D) Summary of data from panel C. SKA-31 extends the duration of the AHP in ATXN1[82Q] Purkinje neurons ($p=0.042$). (E) Representative trace which displays the interspike interval during spontaneous firing of a baseline wild-type Purkinje neuron and (Panel F) ATXN1[8Q] Purkinje neuron in the presence of chlorzoxazone (50 µM) and baclofen (10 µM). (Panel G) Single interspike intervals of baseline wild-type and (Panel H) ATXN1[82Q] Purkinje neurons in the present of chlorzoxazone and baclofen. *$p<0.05$, $p<0.01$, *$p<0.001$, paired Student's t-test. CHZ, chlorzoxazone.

Mice were anesthetized by isoflurane inhalation, decapitated, and brains removed for slice preparation. For measurements of somatic spiking and whole-cell somatic physiology (FIGS. 1-3), slices were prepared in cutting solution at 4° C. (Refs. 1-3, 26, 27; herein incorporated by reference in their entireties). For dendritic calcium spike experiments, slices were prepared in pre-warmed (33° C.) aCSF. Slice preparation at 33° C. for Purkinje neuron recordings has been performed previously (Refs. 28, 29; herein incorporated by reference in their entireties) and results in better preservation of dendritic morphology. Slices were prepared using a vibratome (Leica) to 300 μm thickness. Slices were incubated in 33° C. aCSF bubbled with 5% CO$_2$ and 95% O$_2$ (carbogen) for 45 minutes after sectioning.

Patch-Clamp Recordings

Patch-clamp recordings were performed (Ref 1; herein incorporated by reference in its entirety). Cell-attached and whole-cell recordings were performed at 33° C. in carbogen-bubbled aCSF at a flow rate of 2-3 ml/min 1-5 hours after slice preparation. Recordings were performed using an Axopatch 200B amplifier, Digidata 1440A interface, and pClamp-10 software (MDS analytical technologies, Sunnyvale, Calif.). Data were acquired at 100 kHz in the fast current clamp mode of the amplifier and filtered at 2 kHz. For some dendritic excitability experiments, data were acquired using an Axon Multiclamp 700B amplifier, with voltage data acquired in current-clamp mode with bridge balance compensation and filtered at 2 kHz. Cells were rejected if the series resistance changed by more than 20% over the duration of the recording, or if it exceeded 15 MΩ. Voltage traces were corrected for a 10 mV liquid junction potential. For all recordings involving pharmacologic agents, baseline data was acquired for 5 minutes before introducing agents into the bath. Agents were perfused for up to 15 minutes.

Analysis of Intrinsic Dendritic Excitability

Analysis of intrinsic dendritic excitability was performed (Ref 30; herein incorporated by reference in its entirety). Neurons were held at −80 mV in the whole-cell recording configuration in the presence of tetrodotoxin (1 μM) to block voltage-gated sodium channels. Purkinje neuron somata were then injected with depolarizing current in +50 pA increments until calcium spike events were noted. This amount of injected current was used as a correlate of dendritic excitability for all studies.

Phenotype Analysis

Motor phenotype was analyzed by performance on a rotarod. This study was powered to detect a 25% improvement in motor performance, which was estimated to require at least 8 mice in each group. For all experiments, mice were handled for three consecutive days starting at 25 days of age in order to acclimate to the experimenter and test environment. Mice were then trained on an accelerating rotarod (4 to 40 rpm, at a rate of 0.12 rpm/s) for three days followed by one training day at constant speed (24 rpm). Baseline rotarod performance is variable between individual cohorts of mice, so all experimental groups were represented in each behavioral cohort. Despite baseline differences in performance between cohorts, impaired motor performance was always observed in ATXN1[82Q] mice compared to wild-type controls. Since baseline motor function is variable between cohorts of mice, mice were randomized into groups based on their baseline performance on the final day of training, and all groups were balanced by sex and mean group performance in order to establish a standard baseline within each behavior cohort. Drug or vehicle was then administered via water bottles for the duration of the experiment after the final day of training. Mice were tested for four or five days at a constant speed (24 rpm) starting at 35 days of age for the early time point, and most groups were re-tested at 98 days (14 weeks) of age for the long-term time point. Latency score was recorded as either the time taken before the animal fell off the bar, or if an animal made three full rotations on the rotating bar, to a maximum time of 300 seconds. Mice were maintained with water bottle delivery of drug for the duration of the behavioral experiment. After testing at the late time point, mice were sacrificed and brains preserved for analysis of drug concentrations. The tester remained blind to genotype and treatment condition during experimentation. Performance on the rotarod was analyzed with a two-way repeated-measures ANOVA by trial with Holm-Sidak multiple comparison test.

Water Bottle Delivery of Pharmacologic Agents

Baclofen was dissolved in drinking water at 350 μM for all studies. SKA-31 was dissolved in drinking water at 600 μM for all studies. Since SKA-31 is not easily water-soluble, drinking water also contained 0.05% β-(hydroxypropyl)-cyclodextrin and 40 μL/L of 1N NaOH, and supplemented with up to 8% sucrose. Chlorzoxazone was dissolved in drinking water at 15 mM (Ref 31; herein incorporated by reference in its entirety). Similar to SKA-31, drinking water containing chlorzoxazone also contained 0.05% β-(hydroxypropyl)-cyclodextrin and 40 μL/L of 1N NaOH, and supplemented with up to 8% sucrose. For vehicle treatment, drinking water containing 0.05% β-(hydroxypropyl)-cyclodextrin, NaOH, and sucrose was used. Water bottles were changed twice weekly. Mice were treated with water bottles beginning at 28 days of age and maintained on water bottles for the duration of the experiment.

Mass Spectrometry of Brain Tissue and Blood Plasma

LC/MS analysis for SKA-31, chlorzoxazone and baclofen was performed with a Waters Acquity UPLC (Waters, N.Y. USA) interfaced to a TSQ Quantum Access Max mass spectrometer (MS) (Thermo Scientific, Waltham, Mass., USA).

For SKA-31, commercial SPE cartridges (Hypersep C18, 100 mg, 1 mL, Thermo Scientific) were conditioned with acetonitrile, 2×1 mL, followed by water 2×1 mL. After loading the SPE cartridges with plasma samples, they were washed with 2 mL of 20% acetonitrile in water and eluted with 2 mL of acetonitrile. Elute fractions were evaporated to dryness, reconstituted with 200 μL acetonitrile and used for LC-MS analysis. For brain samples 200 mg of tissue were homogenized thoroughly in 4.0 mL of acetonitrile using a T25 digital ULTRA-TURRAX homogenizer (IKA Works Inc., NC), centrifuged for 10 min at 4000 rpm, and the supernatant separated and evaporated. The residues were reconstituted in 200 μL acetonitrile and loaded onto the preconditioned SPE cartridges and then eluted as described above. Load and elute fractions were collected and evaporated to dryness. The residues were reconstituted with 200 μL acetonitrile and used for LC-MS analysis on an Acquity UPLC BEH C-18 column 1.7 μM, 2.1×50 mM (Waters) using an isocratic mobile phase (45% acetonitrile and 55% water containing 0.1% formic acid) with a flow rate of 0.25 ml/min. Under these conditions SKA-31 had a retention time of 1.17 min. Mass conditions: heated electrospray ionization (HESI II) in positive ion mode, capillary temperature 350° C., vaporizer temperature: 325° C., spray voltage 4000 V, sheath gas pressure ($N_2$) 30 units, SKA-31 was analyzed by the selective reaction monitoring (SRM) transition of its molecular ion peak 201.04 (M+1) into 115.16 m/z.

Baclofen was extracted by plasma precipitation; 1.0 mL ethanol was added to 200 μL plasma and the resulting precipitate vortexed for 30 sec. Samples were the centrifuged for 5 min at 4000 rpm, the supernatant separated and evaporated to dryness under a constant air flow. The residues were reconstituted with 200 μL water:acetonitrile (1:1) and used for LC-MS analysis. For brain samples 200 mg of tissue were homogenized thoroughly in 4.0 mL of acetonitrile using a T25 digital ULTRA-TURRAX® homogenizer, centrifuged for 10 min at 4000 rpm, and the supernatant separated and evaporated. The residues were reconstituted with 200 μL acetonitrile and used for LC-MS analysis on an Acquity UPLC BEH C-8 column 1.7 μM, 2.1×150 mM (Waters) using an isocratic mobile phase (10% acetonitrile and 90% water containing 0.1% formic acid) with a flow rate of 0.20 ml/min. Under these conditions baclofen had a retention time of 2.1 min. Mass conditions: Heated electrospray ionization (HESI II) in positive ion mode, capillary temperature 300° C., vaporizer temperature: 250° C., spray voltage 3000 V, sheath gas pressure ($N_2$) 35 units, baclofen was analyzed by the SRM transition of its molecular ion peak 214.04 (M+1) into 151.03 m/z.

Chlorzoxazone was extracted by plasma precipitation; 3.0 mL acetonitrile was added to 200 μL, plasma, diluted with 200 μL of water and the resulting precipitate vortexed for 30 sec. Samples were then centrifuged for 5 min at 4000 rpm, the supernatant separated and evaporated to dryness. The residues were reconstituted with 200 μL water:acetonitrile (1:1) and used for LC-MS analysis. For brain samples 200 mg of tissue were homogenized thoroughly in 4.0 mL of acetonitrile using a T25 digital ULTRA-TURRAX® homogenizer, centrifuged for 10 min at 4000 rpm, and the supernatant separated and evaporated. The residues were reconstituted with 200 μL acetonitrile and used for LC-MS analysis on a Acquity UPLC BEH C-18 column 1.7 μM, 2.1×50 mM (Waters) using mobile phase gradient varying from of 5% acetonitrile and 95% water both containing 0.1% formic acid (0-1.5 min.) to 30% acetonitrile and 70% water (1.51-5.0 min.) and back to 5% acetonitrile and 95% water (5.01-6.0 min.) with a flow rate of 0.20 ml/min. Under these conditions chlorzoxazone had a retention time of 2.7 min. Mass conditions: Heated electrospray ionization (HESI II) in negative ion mode, capillary temperature 300° C., vaporizer temperature: 250° C., spray voltage 3000 V, sheath gas pressure ($N_2$) 25 units, chlorzoxazone was analyzed by the SRM transition of its molecular ion peak 167.99 (M-1) into 132.07 m/z.

Review of Patient Charts

Approval for retrospective review of patient charts seen through the University of Michigan Ataxia Clinic was submitted to the Institutional Review Board (IRB) for human subjects. The IRB reviewed the study application and determined that it is exempt from ongoing IRB review, per the federal exemption category: Exemption #4 of the 45 CFR 46.101.(b): Research involving the collection or study of existing data, documents, records, pathological specimens, or diagnostic specimens, if these sources are publicly available or if the information is recorded by the investigator in such a manner that subjects cannot be identified, directly or through identifiers linked to the subjects. Approval was granted for review of records through December 2016.

Statistical Analysis

Statistical significance for electrophysiology data was assessed by either unpaired Student's t-test, paired Student's t-test, or Fisher's exact test with Bonferroni post-correction for multiple comparisons. For behavioral studies, a two-way ANOVA with Holm-Sidak post-correction for multiple comparisons was used. Data were considered significant if the adjusted p<0.05. Data are expressed as mean±standard error of the mean, unless otherwise specified. Data were analyzed using SigmaPlot (Systat Software, Inc.), GraphPad Prism (GraphPad Software, Inc.) and Excel (Microsoft Corp.).

Results

Alterations in Purkinje neuron spiking have been demonstrated previously in the ATXN1[82Q] mouse model of SCA1 (Ref 2; herein incorporated by reference in its entirety). In order to confirm these findings, cell-attached electrophysiological recordings were performed in acute cerebellar slices from Purkinje neurons from ATXN1[82Q] and wild-type mice at 5 weeks of age (FIG. 1A-B). As demonstrated previously, a significant portion of ATXN1 [82Q] Purkinje neurons displayed an absence of repetitive spiking when compared to wild-type neurons, which uniformly displayed repetitive spiking (FIG. 1C; firing frequency 52.2±5.6 Hz, coefficient of variation of spiking 0.112±0.008). In the whole-cell recording configuration, these non-firing cells showed a depolarized membrane potential of −41 mV (FIG. 1D), similar to what was previously described (Ref 2; herein incorporated by reference in its entirety). These alterations in membrane excitability are associated with a reduction in the amplitude of the afterhyperpolarization (AHP) of the action potential (FIG. 1E-F), which is generated by calcium-activated potassium channels (Refs. 2, 32, 33; herein incorporated by reference in its entirety). Since loss of potassium channels is associated with increased dendritic excitability (Ref 30; herein incorporated by reference in its entirety), experiments were conducted during development of embodiments herein to determine whether Purkinje neuron dendrites from ATXN1[82Q] mice were hyperexcitable. Purkinje neurons were held in the whole-cell recording configuration at −80 mV in the presence of tetrodotoxin (TTX, 1 µM) in order to block voltage-gated sodium channels, and were injected with incremental steps of depolarizing current until dendritic calcium spikes were detected. In response to depolarizing current injection, ATXN1[82Q] Purkinje neurons displayed a lower threshold to evoke dendritic calcium spikes, a correlate of increased dendritic excitability (FIG. 1G-I) (Ref 20; herein incorporated by reference in its entirety). Input resistance was not different between wild-type and ATXN1[82Q] Purkinje neurons. Therefore, Purkinje neurons from ATXN1[82Q] mice exhibit a phenotype of increased membrane excitability resulting in both altered spiking and increased dendritic excitability in association with membrane depolarization and a reduction in the amplitude of the AHP.

Alterations in Purkinje neuron spiking in ATXN1[82Q] mice are associated with reductions in expression and function of large-conductance calcium activated potassium (BK) channels and subthreshold-activated potassium channels (Ref 2; herein incorporated by reference in its entirety). In order to determine whether the alterations in physiology which accompany these changes in channel function can be improved pharmacologically, a targeted screen was performed of potassium channel-activating compounds with known roles in membrane repolarization or increasing AHP amplitude. A combination of chlorzoxazone and baclofen restored tonic spiking to non-firing ATXN1[82Q] Purkinje neurons in acute cerebellar slices (FIG. 2B). Chlorzoxazone is a known activator of calcium-activated potassium ($K_{Ca}$) channels, both BK and the related small-conductance calcium activated potassium (SK) channel (refs, 31, 34-36; herein incorporated by reference in their entireties). Baclofen, a GABAB agonist, potentiates a subthreshold-activated potassium channel current in Purkinje neurons likely mediated by the G-protein-coupled inwardly rectifying potassium (GIRK) channels (Ref 37; herein incorporated by reference in its entirety). In order to confirm whether $K_{Ca}$ channels are a target for restored spiking in ATXN1[82Q] Purkinje neurons, other known activators of $K_{Ca}$ channels were tested in the presence of baclofen to determine their ability to restore spiking. Spiking was restored in ATXN1 [82Q] Purkinje neurons that displayed no spontaneous spiking when co-perfused with SKA-31 (FIG. 2C) or 1-EBIO (FIG. 2D), two known $K_{Ca}$ channel activators (Ref 38,39; herein incorporated by reference in its entirety), and baclofen (FIG. 2E). The firing frequency that was restored was, however, significantly lower than what is normally seen in wild-type Purkinje neurons (Chlorzoxazone+baclofen, 7.25±3.21 Hz; SKA-31+baclofen, 10.13±1.86 Hz; 1-EBIO+ baclofen, 2.86±0.54 Hz). Neither chlorzoxazone alone nor baclofen alone consistently restores spiking in non-firing ATXN1[82Q] Purkinje neurons (FIG. 2E). This inmdicates that $K_{Ca}$ and subthreshold activated potassium channels must be targeted simultaneously in order to restore spiking in non-firing ATXN1[82Q] Purkinje neurons.

In order to determine the mechanism by which potassium channel activators restore spiking, the changes in membrane potential produced by these pharmacological agents were examined. In the whole-cell configuration of the patch-clamp technique, baclofen (10 µM) repolarized the membrane potential of depolarized ATXN1[82Q] Purkinje neurons from −41 mV to −52 mV (FIG. 3A). A combination of TTX and cadmium, to respectively block voltage-gated sodium and calcium channels, restored the normal resting membrane potential of ATXN1[82Q] Purkinje neurons (FIG. 3A). These results indicate that subthreshold-activated potassium channels contribute in part to the depolarized potential of ATXN1[82Q] Purkinje neurons. The SK channel-activating compound SKA-31 extended the duration of the AHP in ATXN1[82Q] Purkinje neurons, indicating that $K_{Ca}$-activating compounds (FIG. 2) act on the AHP to support repetitive spiking (FIG. 3C-D). The net effect of baclofen and chlorzoxazone was to greatly enhance repolarization during the interspike interval (FIG. 3E-H). However, the duration of the AHP is extended in ATXN1[82Q] Purkinje neurons perfused with chlorzoxazone and baclofen, consistent with the reduced firing frequencies in cells whose spiking is restored (FIG. 2B-E). This indicates that increasing the amplitude of the AHP through activation of $K_{Ca}$ channels, in addition to membrane repolarization through activation of subthreshold-activated potassium channels, is necessary to facilitate repetitive spiking in depolarized ATXN1[82Q] Purkinje neurons.

Experiments were conducted during development of embodiments herein to determine whether agents which restore spiking could improve motor impairment in ATXN1 [82Q] mice. In order to confirm oral absorption of chlorzoxazone, SKA-31, and baclofen, mass spectrometry analysis of whole brain and plasma samples was performed following administration of these agents through drinking water. All three agents achieved significant brain and plasma levels (SKA-31 brain 1.83±1.30 µM, SKA-31 plasma 39.39±8.05 nM; chlorzoxazone brain 4.80±1.72 µM, chlorzoxazone plasma 4.41±2.05 µM; baclofen brain 377.35±58.50 nM, baclofen plasma 3.06±0.51 µM) that reached concentrations previously shown to be important for engagement of their respective targets (FIG. 4B-D) (Refs. 31, 37, 38; herein incorporated by reference in their entireties), although the achieved dose of SKA-31 is lower than the maximal concentration achieved through intraperitoneal injection (Ref 38; herein incorporated by reference in its entirety). These agents were therefore administered through drinking water in order to explore the relationship between their ability to improve Purkinje neuron physiology in cerebellar slices and ameliorate motor dysfunction.

Figure 4:
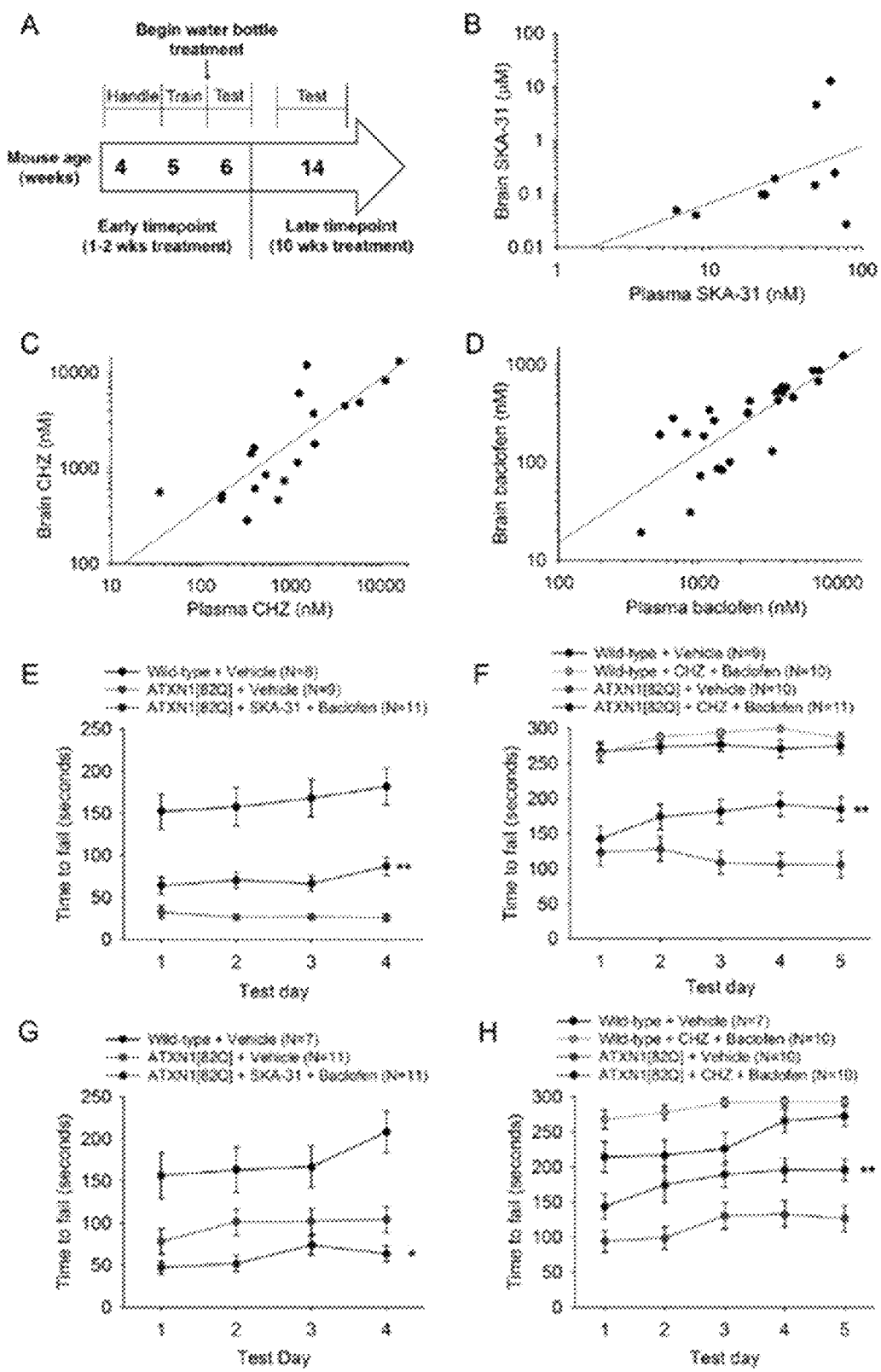
FIG. 4, Panels A-H. Chlorzoxazone and baclofen, but not SKA-31 and baclofen, sustains improvement in motor dysfunction in ATXN1[82Q] mice. (Panel A) Drug administration and behavioral testing paradigm. (Panel B) Correlated brain and plasma levels of SKA-31 are seen after administration through drinking water ($R^2=0.1337$). (Panel C) Correlated brain and plasma levels of chlorzoxazone are seen after administration through drinking water ($R^2=0.8904$). (Panel D) Correlated brain and plasma levels of baclofen are present after administration through drinking water ($R^2=0.8591$). (Panel E) After one week of treatment, SKA- 31+ baclofen improves motor performance in ATXN1[82Q] mice ($F(2, 113)=15.76$, $p<0.0001$) (Wild-type+Vehicle vs ATXN1 [82Q]+Vehicle $p<0.0001$; Wild-type+Vehicle vs ATXN1[82Q]+SKA-31+Baclofenp<0.0001; ATXN1[82Q]+ Vehicle vs ATXN1[82Q]+SKA-31+Baclofen $p=0.004$). (Panel F) After one week of treatment, chlorzoxazone+ baclofen improves motor performance in ATXN1[82Q] mice ($F(3, 156)=42.23$, $p<0.0001$) (Wild-type+Vehicle vs Wild-type+Chlorzoxazone+Baclofen $p=0.9726$; Wild-type+ Vehicle vs ATXN1[82Q]+Vehiclep<0.0001; Wild-type+Vehicle vs ATXN1[82Q]+Chlorzoxazone+Baclofen $p<0.0001$; Wild-type+Chlorzoxazone+Baclofen vs ATXN1[82Q]+Vehicle $p<0.0001$; Wild-type+Chlorzoxazone+Baclofen vs ATXN1 [82Q]+Chlorzoxazone+Baclofen $p<0.0001$; ATXN1 [82Q]+Vehicle vs ATXN1[82Q]+Chlorzoxazone+Baclofenp=0.0036). (Panel G) After 10 weeks of treatment, mice treated with SKA-31+baclofen show worsened motor performance compared to vehicle-treated controls ($F(2, 109)= 36.73$, $p<0.0001$) (Wild-type vs ATXN1 [82Q]+Vehicle $p=0.0005$; Wild-type vs ATXN1[82Q]+SKA-31+Baclofen $p<0.0001$; ATXN1[82Q]+Vehicle vs ATXN1[82Q]+ SKA-31+Baclofen $p=0.0408$). (Panel H) After 10 weeks of treatment, ATXN1[82Q] mice treated with chlorzoxazone+ baclofen display sustained improvement in motor performance compared to vehicle-treated controls ($F(3, 144)= 29.43$, $p<0.0001$) (Wild-type+Vehicle vs Wild-type+Chlorzoxazone+Baclofenp=0.0292; Wild-type+Vehicle vs ATXN1[82Q]+Vehicle $p<0.0001$; Wild-type+Vehicle vs ATXN1[82Q]+Chlorzoxazone+Baclofenp=0.0097; Wild-type+Chlorzoxazone+Baclofen vs ATXN1 [82Q]+Vehicle $p<0.0001$; Wild-type+Chlorzoxazone+Baclofen vs ATXN1 [82Q]+Chlorzoxazone+Baclofenp<0.0001; ATXN1[82Q]+ Vehicle vs ATXN1[82Q]+Chlorzoxazone+Baclofen $p= 0.0029$). *$p<0.05$, **$p<0.01$, two-way ANOVA with Holm-Sidak post-test. CHZ, chlorzoxazone.

ATXN1[82Q] and age-matched wild-type control mice were administered either chlorzoxazone (15 mM in drinking water) and baclofen (350 µM in drinking water) or SKA-31 (600 µM in drinking water) and baclofen (350 µM in drinking water) at 5 weeks, at the onset of motor dysfunction (Refs. 2, 4; herein incorporated by reference in their entireties) and tested for both short- and long-term improvement in motor dysfunction. After one week of treatment, SKA-31 and baclofen significantly improved motor performance in ATXN1[82Q] mice when compared to vehicle-treated controls (FIG. 4E). Similarly, following one week of treatment with a combination of chlorzoxazone and baclofen there was a significant improvement in motor performance in ATXN1 [82Q] mice (FIG. 4F). These results indicate that at a time point corresponding to the loss of spiking in ATXN1[82Q] Purkinje neurons, agents which restore spiking are able to improve motor dysfunction.

It has been observed that spiking in ATXN1[82Q] Purkinje neurons is restored due to homeostatic remodeling associated with Purkinje neuron atrophy (Ref 2; herein incorporated by reference in its entirety). In order to determine whether potassium channel activators continue to provide benefit at a stage of disease when there is significant Purkinje neuron atrophy, mice were administered these compounds through drinking water from 5 weeks of age until 14 weeks of age and motor performance was tested. ATXN1[82Q] mice treated with SKA-31 and baclofen displayed impaired motor function at 14 weeks of age (FIG. 4G), while ATXN1[82Q] mice treated with chlorzoxazone and baclofen showed a sustained improvement in motor performance (FIG. 4H). These data indicate that although SKA-31 and chlorzoxazone, in combination with baclofen, have a similar role in restoring spiking, chlorzoxazone but not SKA-31 engages a different target which allows for maintained improvement in motor dysfunction.

Figure 5:
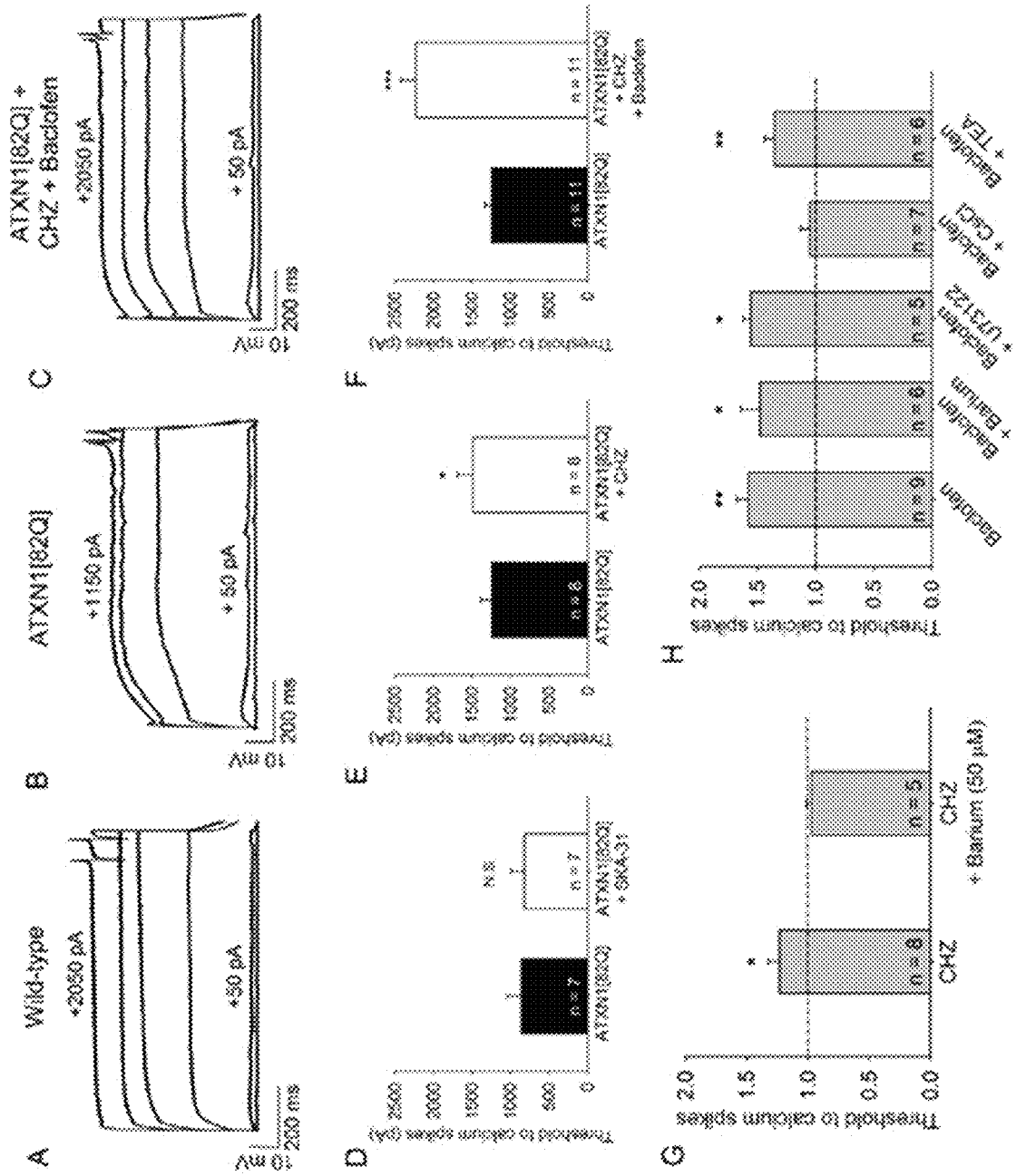
FIG. 5, Panels A-H. Chlorzoxazone and baclofen reduce dendritic hyperexcitability in ATXN1[82Q] mice by activating subthreshold-activated potassium channels. (Panel A) Representative trace of dendritic calcium spikes from a wild-type Purkinje neuron, (Panel B) ATXN1[82Q] Purkinje neuron at baseline, and (Panel C) the same ATXN1[82Q] Purkinje neuron treated with chlorzoxazone (50 µM) and baclofen (2 µM). (Panel D) SKA-31 (10 µM) does not reduce dendritic hyperexcitability in ATXN1[82Q] Purkinje neurons ($p=0.376$). (Panel E) Chlorzoxazone (50 µM) reduces dendritic hyperexcitability in ATXN1[82Q] Purkinje neurons ($p=0.025$). (Panel F) Chlorzoxazone (50 µM) and baclofen (2 µM) co-administration further reduces dendritic excitability in ATXN1[82Q] Purkinje neurons ($p<0.001$). (Panel G) Barium (50 µM) occludes the effect of chlorzoxazone on dendritic excitability ($p=0.778$). (Panel H) Barium (500 µM, $p=0.012$), U73122 (10 µM in recording pipette, $p=0.014$), and TEA (1 mM, $p=0.009$) do not occlude the effect of baclofen on dendritic excitability, but cesium chloride (140 mM in the recording pipette) does occlude the effect of baclofen on dendritic excitability ($p=0.356$), in ATXN1[82Q] Purkinje neurons. *$p<0.05$, $p<0.01$, *$p<0.001$, paired Student's t-test. CHZ, chlorzoxazone.

Dendritic hyperexcitability begins at the onset of motor dysfunction in ATXN1[82Q] Purkinje neurons and is persistently elevated in spite of relative normalization of spiking in atrophic ATXN1[82Q] Purkinje neurons (Ref 10; herein incorporated by reference in its entirety). ATXN1 [82Q] Purkinje neurons required a significantly lower amount of injected current to elicit dendritically-generated calcium spikes than wild-type neurons (FIG. 5A-B). Chlorzoxazone (FIGS. 5E and 5G) but not SKA-31 (FIG. 5D) significantly increased the threshold of injected current necessary to elicit dendritic calcium spikes in ATXN1[82Q] Purkinje neurons. The combination of chlorzoxazone and baclofen restored dendritic excitability to near wild-type levels (FIG. 5F), indicating that this combination of compounds improves both spiking and dendritic hyperexcitability in ATXN1[82Q] Purkinje neurons. Chlorzoxazone and baclofen did not alter input resistance in these recordings.

SKA-31 is a highly selective activator of SK2 and IK channels (Ref 38; herein incorporated by reference in its entirety). The targets of chlorzoxazone are, however, largely unknown. Experiments were conducted during development of embodiments herein to determine the ion-channel targets of chlorzoxazone's effect on dendritic excitability. Chlorzoxazone does not likely act through SK channels in the dendrites, since SKA-31 had no effect on dendritic excitability. When tested in the presence of barium (50 μM), which at this dose selectively blocks subthreshold-activated inwardly-rectifying potassium ($K_{ir}$) channels (Refs. 2, 41-45; herein incorporated by reference in their entireties), the effect of chlorzoxazone on reducing dendritic excitability was prevented (FIG. 5G). This indicates that chlorzoxazone activates $K_{ir}$ channels in the dendrites of ATXN1[82Q] Purkinje neurons to reduce dendritic hyperexcitability.

Experiments were also conducted during development of embodiments herein to determine the molecular target of baclofen on dendritic excitability. Although baclofen is known to activate G-protein coupled $K_{ir}$ channels (GIRK) in Purkinje neurons (Ref 37; herein incorporated by reference in its entirety), barium (500 μM) did not prevent the effect of baclofen in reducing the threshold to elicit dendritic calcium spikes (FIG. 5H), indicating that baclofen does not modulate dendritic excitability through these channels in ATXN[82Q] Purkinje neurons. Since baclofen may act downstream of metabotropic glutamate receptor (mGluR) signaling (Ref 46; herein incorporated by reference in its entirety), experiments were conducted during development of embodiments herein to determine whether the effect of baclofen is dependent on mGluR activation. U73122, a phospholipase C inhibitor, did not prevent the effect of baclofen on dendritic excitability (FIG. 5H), indicating that the effect of baclofen does not require mGluR activation in this context (Ref 47; herein incorporated by reference in its entirety). Cesium, a non-selective potassium channel inhibitor, prevents the effect of baclofen when included in the recording pipette, confirming that baclofen activates a potassium channel conductance in ATXN1[82Q] Purkinje neurons (FIG. 5H). Tetraethlyammonium (TEA) does not block the effect of baclofen (FIG. 5H), excluding Kv3 and BK channels as a target. These data indicate that baclofen activates a relatively barium-insensitive subthreshold-activated potassium channel in ATXN1[82Q] Purkinje neuron dendrites to reduce dendritic hyperexcitability.

Figure 6:
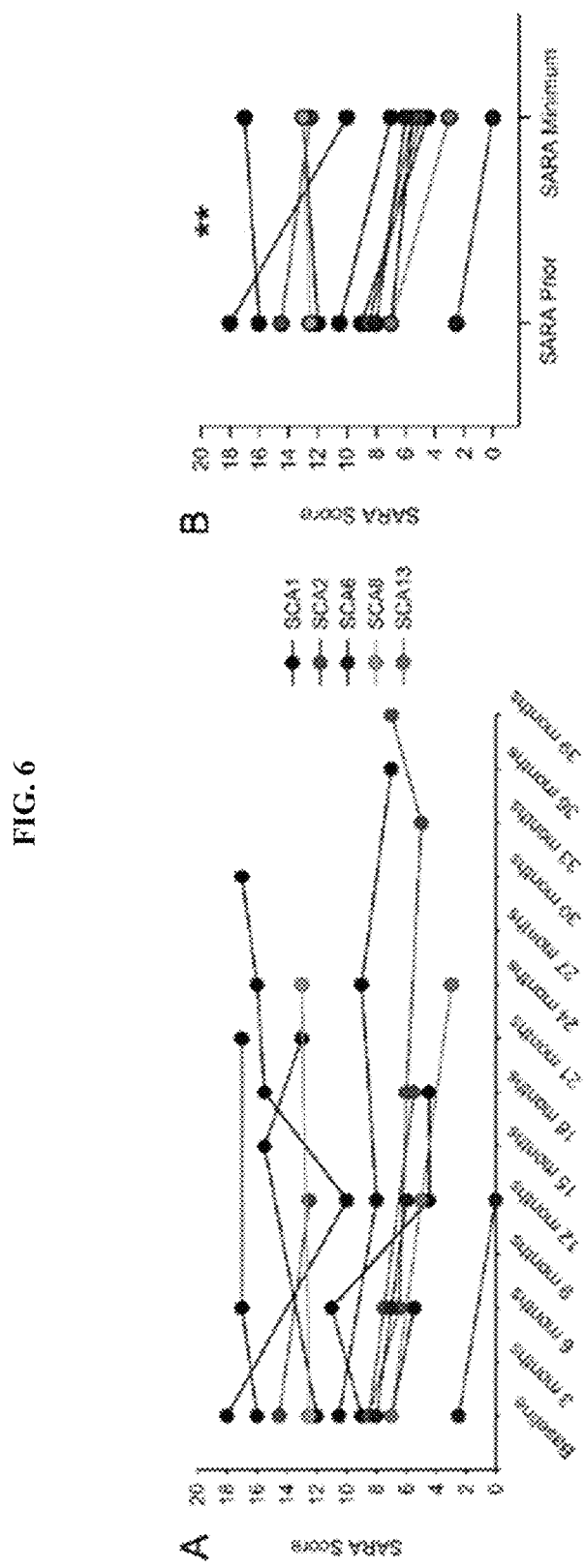
FIG. 6, Panels A-B. Chlorzoxazone and baclofen co-administration is tolerated in SCA patients and improves symptoms. (Panel A) SARA scores were obtained for each patient prior to beginning treatment with chlorzoxazone and baclofen, and subsequent SARA scores were obtained at follow-up visits. SARA scores are only displayed for patients who could tolerate treatment and had at least one follow-up visit. (Panel B) SARA scores are displayed prior to treatment and at the time point which showed a minimum SARA score after beginning treatment (p=0.004). **p<0.01, paired Student's t-test.
Figure 7:
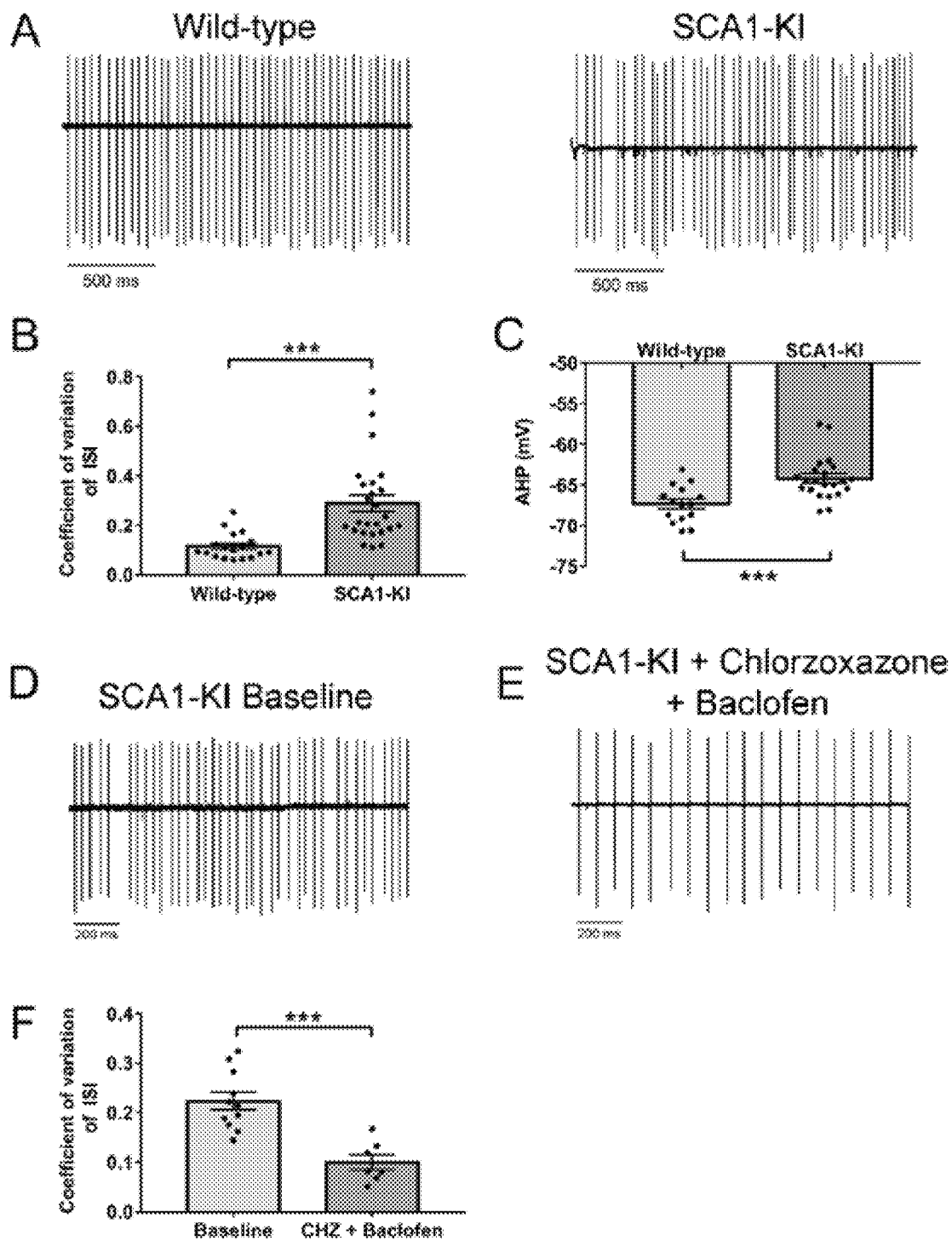
FIG. 7, Panels A-F. Purkinje neuron spiking is significantly abnormal in SCA1[Q154] (SCAT-KI) mice. Chlorzoxazone/Baclofen restore regularity of spiking in SCAT-KI Purkinje neurons (Panel A). Spiking in a wild-type Purkinje cell at 14 weeks: regularity of spiking in WT (left); spiking is very irregular in age matched SCAT-KI Purkinje cells (right) (Panel B) Summary of the irregularity in spiking in SCAT-KI PCs as represented by an increase in the coefficient of variation of the interspike interval. p<0.001. (Panel C) The amplitude of the AHP is reduced consistent with reduced KCa channel function. p<0.001. (Panel D) Irregular Purkinje neuron spiking in cerebellar slices from SCAT-KI mice is improved in E. by perfusion of 50 µM chlorzoxazone and 2 µM baclofen. There is a reduction in firing frequency with this combination as seen in SCA1-Tg mice F. A combination of baclofen/chlorzoxazone improves Purkinje cell spiking regularity to wild-type levels (compare Panels B and F).

Chlorzoxazone and baclofen are both FDA-approved compounds to reduce muscle spasticity, and chlorzoxazone has previously been demonstrated to reduce downbeat nystagmus (Ref 48; herein incorporated by reference in its entirety). In mouse models of SCA1, SCA2, and SCA6, ataxias which all display prominent Purkinje neuron involvement, potassium channel dysfunction is present (Refs. 1, 2, 19; herein incorporated by reference in its entirety). Also, since pyramidal signs are a feature of many SCAs, and some patients with SCA6 can exhibit downbeat nystagmus, patients seen through the University of Michigan Ataxia Clinic with either pyramidal signs or downbeat nystagmus were offered a trial of baclofen and chlorzoxazone. All patients were interested in a trial of the medications. Since the American Geriatrics Society discourages combining muscle relaxants through the updated Beers criteria (Ref 49; herein incorporated by reference in its entirety), it is important to know whether the combination of baclofen and chlorzoxazone is tolerated by patients with ataxia. In order to determine whether the combination of chlorzoxazone and baclofen is tolerated by SCA patients, medical records were reviewed of patients with SCA1 and other SCAs with prominent Purkinje neuron involvement who were seen through the Ataxia Clinic. Patients were started on one agent at a time and the dose was gradually increased to a target dose of 10 mg TID for baclofen and 500 mg TID of chlorzoxazone. If patients could not tolerate 500 mg TID of chlorzoxazone, a lower dose of 250 mg TID was attempted. Patients for whom follow up information was present are listed in Table 1. Of 17 patients, 4 could not tolerate one of either baclofen or chlorzoxazone due to side effects (Table 1). The Scale for the Assessment and Rating of Ataxia (SARA) is a validated clinical measure of ataxia, with higher scores indicating more prominent ataxia (Ref 50; herein incorporated by reference in its entirety). SARA scores were recorded for all patients prior to beginning treatment and were assessed during subsequent visits. The average interval between visits for patients in the Ataxia Clinic is 6 months. Patients reported subjective improvement in symptoms over time which was corroborated by the reduction in SARA score for individual patients (FIG. 6A). Patients reported improvement in symptoms that was delayed by weeks, after achieving maximum tolerated doses of medication. In order to assess the maximum benefit, initial SARA scores were compared to minimum SARA scores subsequent to initiation of chlorzoxazone and baclofen. The SARA score subsequent to initiation of chlorzoxazone and baclofen was significantly lower than the score prior to initiating medication (FIG. 6B). Overall, these results indicate that chlorzoxazone and baclofen co-administration is tolerated and improves symptoms in forms of SCA with prominent cerebellar Purkinje neuron involvement.

TABLE 1

Summary of SCA patients treated with baclofen and chlorzoxazone.

| Genotype | Repeat size | Sex | Age | Dosage | Other comments |
|---|---|---|---|---|---|
| SCA1 | 52 | M | 29 | Baclofen 40 mg BID, Chlorzoxazone 750 mg BID | |
| SCA1 | 54 | M | 39 | Baclofen 10 mg TID, Chlorzoxazone 500 mg TID | |
| SCA1 | N/D* | F | 67 | Chlorzoxazone 250 mg once daily | Could not tolerate; Chlorzoxazone made swallowing worse |
| SCA1 | 52 | F | 36 | Baclofen 10 mg TID, Chlorzoxazone 500 mg TID | Could not tolerate due to nausea |
| SCA1 | 52 | F | 29 | Baclofen 20 mg BID, Chlorzoxazone 750 mg BID | |
| SCA1 | 53 | M | 35 | Baclofen 30 mg TID, Chlorzoxazone 500 mg TID | |
| SCA1 | 43 | F | 62 | Baclofen 10 mg TID, Chlorzoxazone 250 mg TID | |
| SCA1 | 46 | F | 58 | Baclofen 10 mg TID, Chlorzoxazone 250/500 mg | |
| SCA2 | 38 | M | 50 | Baclofen 20 mg TID, Chlorzoxazone 500 mg TID | |
| SCA2 | 38 | M | 67 | Baclofen 10 mg TID, Chlorzoxazone 500 mg TID | |
| SCA2 | 43 | M | 24 | Baclofen 20 mg TID, Chlorzoxazone 500 mg TID | |
| SCA6 | 21 | M | 57 | Baclofen 10 mg TID, Chlorzoxazone 500 mg TID | |
| SCA6 | 22 | M | 65 | Baclofen 10 mg BID, Chlorzoxazone 500 mg BID | Substantial improvement in downbeat nystagmus |
| SCA8 | 1268 | F | 79 | Chlorzoxazone 500 mg BID | Could not tolerate due to worsened speech |
| SCA8 | 108 | F | 62 | Baclofen 10 mg TID | Could not tolerate; Baclofen caused weakness |
| SCA8 | N/D | M | 51 | Baclofen 10 mg TID, Chlorzoxazone 500 mg TID | Improvement in swallowing and speech due to improvement in dystonia |
| SCA13 | n/a | F | 56 | Baclofen 20 mg TID, Chlorzoxazone 500 mg TID | |

*N/D: not documented

REFERENCES

The following references, some of which are cited above by number, are herein incorporated by reference in their entireties.

1. Dell'Orco J M, Pulst S M, Shakkottai V G. Potassium channel dysfunction underlies Purkinje neuron spiking abnormalities in spinocerebellar ataxia type 2. Human Molecular Genetics. 2017.
2. Dell'Orco J M, Wasserman A H, Chopra R, et al. Neuronal Atrophy Early in Degenerative Ataxia Is a Compensatory Mechanism to Regulate Membrane Excitability. J Neurosci. 2015 Aug. 12; 35(32):11292-307.
3. Shakkottai V G, do Carmo Costa M, Dell'Orco J M, Sankaranarayanan A, Wulff H, Paulson H L. Early changes in cerebellar physiology accompany motor dysfunction in the polyglutamine disease spinocerebellar ataxia type 3. J Neurosci. 2011 Sep. 7; 31(36):13002-14.
4. Hansen S T, Meera P, Otis T S, Pulst S M. Changes in Purkinje cell firing and gene expression precede behavioral pathology in a mouse model of SCA2. Hum Mol Genet. 2013 Jan. 15; 22(2):271-83.
5. Ferrer I, Genis D, Davalos A, Bernado L, Sant F, Serrano T. The Purkinje cell in olivopontocerebellar atrophy. A Golgi and immunocytochemical study. Neuropathol Appl Neurobiol. 1994 February; 20(1):38-46.
6. Durr A. Autosomal dominant cerebellar ataxias: polyglutamine expansions and beyond. Lancet Neurol. 2010 September; 9(9):885-94.
7. Bean B P. The action potential in mammalian central neurons. Nat Rev Neurosci. 2007 June; 8(6):451-65.
8. Raman I M, Bean B P. Ionic currents underlying spontaneous action potentials in isolated cerebellar Purkinje neurons. J Neurosci. 1999 Mar. 1; 19(5):1663-74.
9. Raman I M, Bean B P. Properties of sodium currents and action potential firing in isolated cerebellar Purkinje neurons. Ann N Y Acad Sci. 1999 Apr. 30; 868:93-6.
10. Chopra R, Wasserman A H, Bushart D D, Dell'Orco J M, Shakkottai V G. Increased dendritic excitability and calcium-dependent PKC activation: a novel mechanism underlying Purkinje neuron dendritic degeneration in cerebellar ataxias. Ann Neurol. 2016; 80(s20):S33-S4.
11. Staisch J, Du X, Kubota T, de Souza J, Bezanilla F, Gomez C. A novel KNCMA1 mutation associated with progressive cerebellar ataxia. Neurology. 2015 Apr. 6, 2015; 84(14):P2.118.
12. Waters M F, Minassian N A, Stevanin G, et al. Mutations in voltage-gated potassium channel KCNC3 cause degenerative and developmental central nervous system phenotypes. Nat Genet. 2006 April; 38(4):447-51.
13. Duarri A, Jezierska J, Fokkens M, et al. Mutations in potassium channel kcnd3 cause spinocerebellar ataxia type 19. Ann Neurol. 2012 December; 72(6):870-80.
14. Lee Y C, Durr A, Majczenko K, et al. Mutations in KCND3 cause spinocerebellar ataxia type 22. Ann Neurol. 2012 December; 72(6):859-69.
15. van de Leemput J, Chandran J, Knight M A, et al. Deletion at ITPR1 underlies ataxia in mice and spinocerebellar ataxia 15 in humans. PLoS Genet. 2007 June; 3(6):e108.
16. Fogel B L, Hanson S M, Becker E B. Do mutations in the murine ataxia gene TRPC3 cause cerebellar ataxia in humans? Mov Disord. 2015 February; 30(2):284-6.
17. Coutelier M, Blesneac I, Monteil A, et al. A Recurrent Mutation in CACNA1G Alters Cav3.1 T-Type Calcium-Channel Conduction and Causes Autosomal-Dominant Cerebellar Ataxia. Am J Hum Genet. 2015 Nov. 5; 97(5): 726-37.
18. Morino H, Matsuda Y, Muguruma K, et al. A mutation in the low voltage-gated calcium channel CACNA1G alters the physiological properties of the channel, causing spinocerebellar ataxia. Mol Brain. 2015 Dec. 29; 8:89.
19. Jayabal S, Chang H H, Cullen K E, Watt A J. 4-aminopyridine reverses ataxia and cerebellar firing deficiency in a mouse model of spinocerebellar ataxia type 6. Sci Rep. 2016 Jul. 6; 6:29489.
20. Kasumu A W, Hougaard C, Rode F, et al. Selective positive modulator of calcium-activated potassium channels exerts beneficial effects in a mouse model of spinocerebellar ataxia type 2. Chem Biol. 2012 Oct. 26; 19(10): 1340-53.
21. Ristori G, Romano S, Visconti A, et al. Riluzole in cerebellar ataxia: a randomized, double-blind, placebo-controlled pilot trial. Neurology. 2010 Mar. 9; 74(10): 839-45.
22. Romano S, Coarelli G, Marcotulli C, et al. Riluzole in patients with hereditary cerebellar ataxia: a randomised, double-blind, placebo-controlled trial. Lancet Neurol. 2015 October; 14(10):985-91.
23. Doble A. The pharmacology and mechanism of action of riluzole. Neurology. 1996 December; 47(6 Suppl 4):S233-41.
24. Cao Y J, Dreixler J C, Couey J J, Houamed K M. Modulation of recombinant and native neuronal SK channels by the neuroprotective drug riluzole. Eur J Pharmacol. 2002 Aug. 2; 449(1-2):47-54.
25. Burright E N, Clark H B, Servadio A, et al. SCA1 transgenic mice: a model for neurodegeneration caused by an expanded CAG trinucleotide repeat. Cell. 1995 Sep. 22; 82(6):937-48.
26. Shakkottai V G, Chou C H, Oddo S, et al. Enhanced neuronal excitability in the absence of neurodegeneration induces cerebellar ataxia. J Clin Invest. 2004 February; 113(4):582-90.
27. Shakkottai V G, Xiao M, Xu L, et al. FGF14 regulates the intrinsic excitability of cerebellar Purkinje neurons. Neurobiol Dis. 2009 January; 33(1):81-8.
28. Mercer A A, Palarz K J, Tabatadze N, Woolley C S, Raman I M. Sex differences in cerebellar synaptic transmission and sex-specific responses to autism-linked Gabrb3 mutations in mice. Elife. 2016 Apr. 14; 5.
29. Ankri L, Yarom Y, Uusisaari M Y. Slice it hot: acute adult brain slicing in physiological temperature. J Vis Exp. 2014 Oct. 30(92):e52068.
30. Zagha E, Manita S, Ross W N, Rudy B. Dendritic Kv3.3 potassium channels in cerebellar purkinje cells regulate generation and spatial dynamics of dendritic Ca2+ spikes. J Neurophysiol. 2010 June; 103(6):3516-25.
31. Alvina K, Khodakhah K. KCa channels as therapeutic targets in episodic ataxia type-2. J Neurosci. 2010 May 26; 30(21):7249-57.
32. Sausbier M, Hu H, Arntz C, et al. Cerebellar ataxia and Purkinje cell dysfunction caused by Ca2+-activated K+ channel deficiency. Proc Natl Acad Sci USA. 2004 Jun. 22; 101(25):9474-8.
33. Edgerton J R, Reinhart P H. Distinct contributions of small and large conductance Ca2+-activated K+ channels to rat Purkinje neuron function. J Physiol. 2003 Apr. 1; 548(Pt 1):53-69.
34. Liu Y C, Lo Y K, Wu S N. Stimulatory effects of chlorzoxazone, a centrally acting muscle relaxant, on large conductance calcium-activated potassium channels in pituitary GH3 cells. Brain Res. 2003 Jan. 3; 959(1): 86-97.
35. Cao Y, Dreixler J C, Roizen J D, Roberts M T, Houamed K M. Modulation of recombinant small-conductance Ca(2+)-activated K(+) channels by the muscle relaxant chlorzoxazone and structurally related compounds. J Pharmacol Exp Ther. 2001 March; 296(3):683-9.
36. Gao Z, Todorov B, Barrett C F, et al. Cerebellar ataxia by enhanced Ca(V)2.1 currents is alleviated by Ca2+-dependent K+-channel activators in Cacna1a(S218L) mutant mice. J Neurosci. 2012 Oct. 31; 32(44):15533-46.
37. Tabata T, Haruki S, Nakayama H, Kano M. GABAergic activation of an inwardly rectifying K+ current in mouse cerebellar Purkinje cells. J Physiol. 2005 Mar. 1; 563(Pt 2):443-57.
38. Sankaranarayanan A, Raman G, Busch C, et al. Naphtho[1,2-d]thiazol-2-ylamine (SKA-31), a new activator of KCa2 and KCa3.1 potassium channels, potentiates the endothelium-derived hyperpolarizing factor response and lowers blood pressure. Mol Pharmacol. 2009 February; 75(2):281-95.
39. Pedarzani P, Mosbacher J, Rivard A, et al. Control of electrical activity in central neurons by modulating the gating of small conductance Ca2+-activated K+ channels. J Biol Chem. 2001 Mar. 30; 276(13):9762-9.
40. Hourez R, Servals L, Orduz D, et al. Aminopyridines correct early dysfunction and delay neurodegeneration in a mouse model of spinocerebellar ataxia type 1. J Neurosci. 2011 Aug. 17; 31(33):11795-807.
41. Coetzee W A, Amarillo Y, Chiu J, et al. Molecular diversity of K+ channels. Ann N Y Acad Sci. 1999 Apr. 30; 868:233-85.
42. Quayle J M, McCarron J G, Brayden J E, Nelson M T. Inward rectifier K+ currents in smooth muscle cells from rat resistance-sized cerebral arteries. Am J Physiol. 1993 November; 265(5 Pt 1):C1363-70.
43. Sepulveda F V, Pablo Cid L, Teulon J, Niemeyer M I. Molecular aspects of structure, gating, and physiology of pH-sensitive background K2P and Kir K+-transport channels. Physiol Rev. 2015 January; 95(1):179-217.
44. Hibino H, Inanobe A, Furutani K, Murakami S, Findlay I, Kurachi Y. Inwardly rectifying potassium channels: their structure, function, and physiological roles. Physiol Rev. 2010 January; 90(1):291-366.
45. Alagem N, Dvir M, Reuveny E. Mechanism of Ba(2+) block of a mouse inwardly rectifying K+ channel: differential contribution by two discrete residues. J Physiol. 2001 Jul. 15; 534(Pt. 2):381-93.

46. Shuvaev A N, Hosoi N, Sato Y, Yanagihara D, Hirai H. Progressive impairment of cerebellar mGluR signalling and its therapeutic potential for cerebellar ataxia in spinocerebellar ataxia type 1 model mice. J Physiol. 2017 Jan. 1; 595(1):141-64.

47. Hirono M, Yoshioka T, Konishi S. GABA(B) receptor activation enhances mGluR-mediated responses at cerebellar excitatory synapses. Nat Neurosci. 2001 December; 4(12):1207-16.

48. Feil K, Claassen J, Bardins S, et al. Effect of chlorzoxazone in patients with downbeat nystagmus: a pilot trial. Neurology. 2013 Sep. 24; 81(13):1152-8.

49. Society TAG. American Geriatrics Society Updated Beers Criteria for Potentially Inappropriate Medication Use in Older Adults. Journal of the American Geriatrics Society. 2012; 60:616-31.

50. Schmitz-Hubsch T, du Montcel S T, Baliko L, et al. Scale for the assessment and rating of ataxia: development of a new clinical scale. Neurology. 2006 Jun. 13; 66(11):1717-20.

51. Rancz E A, Hausser M. Dendritic spikes mediate negative synaptic gain control in cerebellar Purkinje cells. Proc Natl Acad Sci USA. 2010 Dec. 21; 107(51):22284-9.

52. Power E M, Morales A, Empson R M. Prolonged Type 1 Metabotropic Glutamate Receptor Dependent Synaptic Signaling Contributes to Spino-Cerebellar Ataxia Type 1. J Neurosci. 2016 May 4; 36(18):4910-6.

53. Jacobi H, Bauer P, Giunti P, et al. The natural history of spinocerebellar ataxia type 1, 2, 3, and 6: a 2-year follow-up study. Neurology. 2011 Sep. 13; 77(11):1035-41.

54. Ashizawa T, Figueroa K P, Perlman S L, et al. Clinical characteristics of patients with spinocerebellar ataxias 1, 2, 3 and 6 in the US; a prospective observational study. Orphanet J Rare Dis. 2013 Nov. 13; 8:177.

The invention claimed is:

1. A method of treating a subject suffering from cerebellar ataxia, comprising:
co-administering to a subject an effective amount of baclofen and chlorzoxazone, such that the cerebellar ataxia or symptoms thereof are reduced.

2. The method of claim 1, wherein the subject is human.

3. The method of claim 1, wherein the baclofen and chlorzoxazone are co-formulated in a single pharmaceutical composition.

4. The method of claim 1, wherein the baclofen and chlorzoxazone are separately-formulated in a single pharmaceutical composition.

5. The method of claim 1, wherein the baclofen and chlorzoxazone are in separate pharmaceutical compositions.

6. The method of claim 5, wherein the separate pharmaceutical compositions are co-administered sequentially.

7. The method of claim 6, wherein administrations are separated by a delay of at least 1 hour.

8. The method of claim 6, wherein administrations are separated by a delay of at least 1 day.

9. The method of claim 1, further comprising a step comprising testing the subject cerebellar ataxia.

10. The method of claim 9, further comprising the step of assessing the effectiveness of treatment based upon said testing.

11. The method of claim 10, further comprising adjusting the treatment based on said assessing.

12. The method of claim 11, wherein adjusting the treatment comprises one or more of: altering the dose of baclofen, altering the dose of chlorzoxazone, altering the dosing regimen of baclofen, altering the dosing regimen of chlorzoxazone, or adding additional treatment.

13. The method of claim 1, wherein the baclofen and chlorzoxazone are co-formulated in a single pharmaceutical composition.

14. The method of claim 1, wherein the baclofen and chlorzoxazone are separately-formulated in a single pharmaceutical composition.

* * * * *